US007592302B2

(12) United States Patent
Itakura et al.

(10) Patent No.: US 7,592,302 B2
(45) Date of Patent: Sep. 22, 2009

(54) POWDERS, FLAKES, OR PELLETS CONTAINING SALTS OF A SULFO FATTY ACID ALKYL ESTERS IN HIGH CONCENTRATIONS, PROCESS FOR PRODUCTION THEREOF, GRANULATED DETERGENTS, AND PROCESS FOR PRODUCTION THEREOF

(75) Inventors: Kensuke Itakura, Tokyo (JP); Akitomo Morita, Tokyo (JP); Masahiko Matsubara, Tokyo (JP); Madoka Suwa, Tokyo (JP); Taku Nishio, Tokyo (JP)

(73) Assignee: Lion Corporation, Tokyo (JP)

( * ) Notice: Subject to any disclaimer, the term of this patent is extended or adjusted under 35 U.S.C. 154(b) by 477 days.

(21) Appl. No.: 10/559,999

(22) PCT Filed: Jun. 11, 2004

(86) PCT No.: PCT/JP2004/008563

§ 371 (c)(1),
(2), (4) Date: Dec. 9, 2005

(87) PCT Pub. No.: WO2004/111166

PCT Pub. Date: Dec. 23, 2004

(65) Prior Publication Data

US 2006/0160717 A1 Jul. 20, 2006

(30) Foreign Application Priority Data

Jun. 12, 2003 (JP) ............................ 2003-168185

(51) Int. Cl.
*C11D 17/06* (2006.01)
*C07C 53/00* (2006.01)
*C08H 3/00* (2006.01)
*C11D 1/28* (2006.01)

(52) U.S. Cl. ....................... 510/446; 510/444; 510/457; 510/498; 554/47; 554/83; 554/97; 554/98; 554/99; 554/100; 554/85; 554/96

(58) Field of Classification Search ................ 510/446; 554/47, 86, 97
See application file for complete search history.

(56) References Cited

U.S. PATENT DOCUMENTS

| | | | | | |
|---|---|---|---|---|---|
| 4,416,809 | A | * | 11/1983 | Magari et al. | 510/477 |
| 4,707,289 | A | * | 11/1987 | Ramachandran et al. | 510/294 |
| 5,429,773 | A | * | 7/1995 | Sherry et al. | 510/444 |

(Continued)

FOREIGN PATENT DOCUMENTS

EP 0 384 480 A2 8/1990

(Continued)

OTHER PUBLICATIONS

English language machine translation of JP 2979727 B2, Nov. 1999, Fukutome et al., Patent-family of JP 04348198 A.*

*Primary Examiner*—Mark Eashoo
*Assistant Examiner*—Jane L Stanley
(74) *Attorney, Agent, or Firm*—Birch, Stewart, Kolasch & Birch, LLP

(57) ABSTRACT

A process for producing powder, flakes, or pellets containing α-sulfo fatty acid alkylester salt in high concentrations, the process including: (1) a step of preparing a paste containing α-sulfo fatty acid alkylester salt; (2) a step of aging the thus obtained paste; (3) a step of making the aged paste into flakes or pellets containing equal to or less than 10 wt % of water and then optionally crushing the resulting flakes or pellets into a powder having an average particle diameter of 100-1500 μm; and (4) a step of aging The powder, flakes, or pellets.

11 Claims, 4 Drawing Sheets

U.S. PATENT DOCUMENTS

| | | | | | |
|---|---|---|---|---|---|
| 5,527,489 | A | * | 6/1996 | Tadsen et al. | 510/294 |
| 6,657,071 | B1 | | 12/2003 | Tano et al. | |

FOREIGN PATENT DOCUMENTS

| | | | | |
|---|---|---|---|---|
| EP | 0 572 957 | A2 | | 12/1993 |
| JP | 51-41675 | A | | 4/1976 |
| JP | 4-359098 | A | | 12/1992 |
| JP | 04348198 | A | * | 12/1992 |
| JP | 5-331496 | A | | 12/1993 |
| JP | 6-184592 | A | | 7/1994 |
| JP | 8-16237 | B2 | | 2/1996 |
| JP | 8-157894 | A | | 6/1996 |
| JP | 9-87700 | A | | 3/1997 |
| JP | 9-143500 | A | | 6/1997 |
| JP | 10-88197 | A | | 4/1998 |
| JP | 11-172299 | A | | 6/1999 |
| JP | 2001-64248 | A | | 3/2001 |
| WO | WO 2004/035717 | A1 | * | 4/2004 |

* cited by examiner

POWDERS, FLAKES, OR PELLETS CONTAINING SALTS OF A SULFO FATTY ACID ALKYL ESTERS IN HIGH CONCENTRATIONS, PROCESS FOR PRODUCTION THEREOF, GRANULATED DETERGENTS, AND PROCESS FOR PRODUCTION THEREOF

TECHNICAL FIELD

The present invention relates to powder, flakes, or pellets containing in high concentrations α-sulfo fatty acid alkylester salt which, upon concentration, yields an extremely white powder with reduced odor and improved storage properties, and a process for production thereof. The present invention relates also to a granular detergent and a solid detergent containing the powder, flakes, or pellets, and a process for production thereof.

BACKGROUND ART

An α-sulfo fatty acid alkylester salt usually takes on an aqueous paste upon neutralization. In order to handle it in the form of concentrate or powder, it is necessary to dewater it somehow or the other. There are two typical processes. One consists of dissolving in water an α-sulfo fatty acid alkylester salt and an inorganic powder to give a slurry containing about 20-70 wt % of water and subsequently spray-drying it to give a dry powder, and the other consists of directly mixing together an α-sulfo fatty acid-alkylester salt (in paste form containing 20-30 wt % of water) and an inorganic powder to give desired particles.

The former process yields a powder containing an α-sulfo fatty acid alkylester salt in comparatively high concentrations because it involves a drying step. However, it consumes much energy and gives off much waste gas into the atmosphere, which would increase environmental loads. Consequently, it is getting out of date recently. Moreover, production through a slurry with a high water content poses a problem with hydrolysis.

As compared with the former process, the latter process can be run with less energy consumption and less environmental loads. However, it presents great difficulties in granulation because α-sulfo fatty acid alkylester salt contains a large amount of water and gives a mixture resembling a paste when its content is high. In addition, the high water content also poses a problem with hydrolysis as in the case of spray drying.

In order to address the above-mentioned problems, there have been proposed various processes for concentration and powderization. Among them is a process involving granulation or powderization of highly concentrated anionic surfactant by means of a film evaporator (Japanese Patent Laid-open No. Hei 5-331496). This process, however, tends to give a product which is poor in flowability at 40° C. or above. Moreover, α-sulfo fatty acid alkylester salt is difficult to powderize by crushing at a high temperature immediately after concentration. Another process is designed to produce a granular detergent efficiently without appreciable sticking to the crushing machine by concentrating a slurry containing an anionic surfactant to give a weight containing equal to or less than 10% of water and crushing it after cooling to 20-70° C. (Japanese Patent Laid-open No. Hei 8-157894). However, this process remains the problem with caking under pressure immediately after powderization.

Further another process is designed to produce particles with improved flowability and solubility by concentrating a slurry containing an anionic surfactant to give particles containing equal to or less than 10% of water and having an average particle diameter of 200-1000 μm and then coating the particles with 1-15 wt % of water-insoluble fine powder (Japanese Patent Laid-open No. Hei 9-87700). This process, however, poses a problem with caking under pressure which occurs immediately after granulation. Further another process is designed to use two kinds of evaporators for concentration of anionic surfactant slurry in order to save electric power and prevent discoloration due to thermal degradation (Japanese Patent Laid-open Nos. Hei 10-88197 and Hei 11-172299). The problem with this process is that the resulting powder is poor in flowability and liable to caking under pressure.

DISCLOSURE OF INVENTION

An object of the present invention is to provide powder, flakes, or pellets (which exhibit good properties during storage, such as anti-caking under pressure and flowability) containing α-sulfo fatty acid alkylester salt in high concentrations and to provide a process for production thereof. Despite the high content of α-sulfo fatty acid alkylester salt, the powder, flakes, or pellets have improved color and reduced odor owing to the specific sulfonating method employed. Another object of the present invention is to provide a granular detergent or a solid detergent containing the powder, flakes, or pellets, and to provide a process for production thereof.

The present inventors have found that it is possible to obtain powder, flakes, or pellets with improved color and reduced odor if they are formed from an aged paste obtained by sulfonating a fatty acid alkylester used as a raw material, esterifying the sulfonated product, neutralizing the esterified product, and bleaching the neutralized product. The present inventors have also found that the powder, flakes, or pellets containing α-sulfo fatty acid alkylester salt in high concentrations exhibit good properties (anti-caking under pressure and flowability) during storage if they are aged after they have been formed from a concentrated paste (with a water content equal to or less than 10 wt %) containing α-sulfo fatty acid alkylester salt.

The present invention provides the following.

[1] A process for producing powder, flakes, or pellets containing α-sulfo fatty acid alkylester salt in high concentrations, said process comprising:

(1) a step of preparing a paste containing α-sulfo fatty acid alkylester salt by a series of reactions of sulfonating a fatty acid alkylester with a sulfonating gas by contact with each other, esterifying the sulfonated product with a lower alcohol, neutralizing the esterified product, and bleaching the neutralized product, to give a paste containing α-sulfo fatty acid alkylester salt;

(2) a step of aging the thus obtained paste;

(3) a step of making the aged paste into flakes or pellets containing equal to or less than 10 wt % of water, or a step of making the aged paste into flakes or pellets containing equal to or less than 10 wt % of water and then crushing the resulting flakes or pellets into a powder having an average particle diameter of 100-1500 μm; and (4) a step of aging the powder, flakes, or pellets.

[2] The process as defined in [1] which further comprises a step of mixing the powder, flakes, or pellets with an inorganic powder having an average particle diameter of 0.1-100 μm, in an amount of 1-40 wt % of the powder, flakes, or pellets.

[3] The process as defined in [1] or [2] wherein the fatty acid alkylester has an iodine value equal to or lower than 1.

[4] Powder, flakes, or pellets containing α-sulfo fatty acid alkylester salt in high concentrations, which are obtained by the process defined in any one of [1] to [3].

[5] The process for producing a granular detergent which comprises mixing or granulating the powder, flakes, or pellets obtained by the process defined in any one of [1] to [3] together with a detergent component by any method selected from powder mixing, kneading-crushing, and agitation granulation.

[6] The process for producing a granular detergent which comprises mixing the powder, flakes, or pellets obtained by the process defined in any one of [1] to [3] together with a detergent component and water, to give a slurry containing 20-50 wt % of water, and spray-drying the slurry.

[7] The process for producing a granular detergent which comprises mixing or granulating the granular detergent obtained by the process defined in [5] or [6] further with a detergent component by any method selected from powder mixing, kneading-crushing, and agitation granulation.

[8] The granular detergent obtained by the process defined in any one of [5] to [7].

[9] The process for producing a solid detergent which comprises mixing and kneading the powder, flakes, or pellets obtained by the process defined in any one of [1] to [3] together with a detergent component, to obtain solid detergent.

BEST MODE FOR CARRYING OUT THE INVENTION

Some terms used in the present invention are defined as follows.

"Powder" is a powdery or particulate material having an average particle diameter of 100-1500 μm.

"Flakes" is a flaky material measuring 1-200 mm in length and width and 0.2-5 mm in thickness.

"Pellets" is a cylindrical material formed by an extruder (such as pelleter), having a diameter of about 5-15 mm and an average length of 5-50 mm.

"Containing in high concentrations" means that the powder, flakes, or pellets contain α-sulfo fatty acid alkylester salt in an amount no less than 50 wt % (net), preferably no less than 75 wt % (net).

"Average particle diameter" is the value calculated from the formula below after classification using a sieve and receiving pan. The sieve should preferably be one which is prescribed in JISZ 8801-1:2000 for "Testing sieve, Part 1, metal net sieve". Incidentally, particles having an average particle diameter equal to or smaller than 100 μm were measured by using an apparatus for measuring the particle size distribution by laser light scattering (Model LDSA-1400A, from Tohnichi Computer Applications).

$$\text{Average particle diameter (weight 50\%)} = 10^{(50-(c-d/(\log b-\log a)\times\log b))/(d/(\log b-\log a))}$$

where, a: the opening (in μm) of the first sieve for which the weight frequency is 50% or more.

b: the opening (in μm) of the sieve having an opening one step larger than a μm.

c: the accumulated weight frequency (in %) of samples collected from the receiving pan and the sieves having openings up to a μm.

d: the weight frequency (in %) of samples collected from the sieve having an opening of a μm.

Production Method of Paste Containing α-Sulfo Fatty Acid Alkylester Salt

According to the present invention, the process for producing powder, flakes, or pellets containing α-sulfo fatty acid alkylester salt in high concentrations starts with a first step of preparing a paste containing α-sulfo fatty acid alkylester salt.

(1) The first step includes a series of reactions of sulfonating a fatty acid alkylester with a sulfonating gas by contact with each other, esterifying the sulfonated product with a lower alcohol, neutralizing the esterified product, and bleaching the neutralized product, thereby giving a paste containing α-sulfo fatty acid alkylester salt. The bleaching may be carried out before neutralizing.

Figure 1:
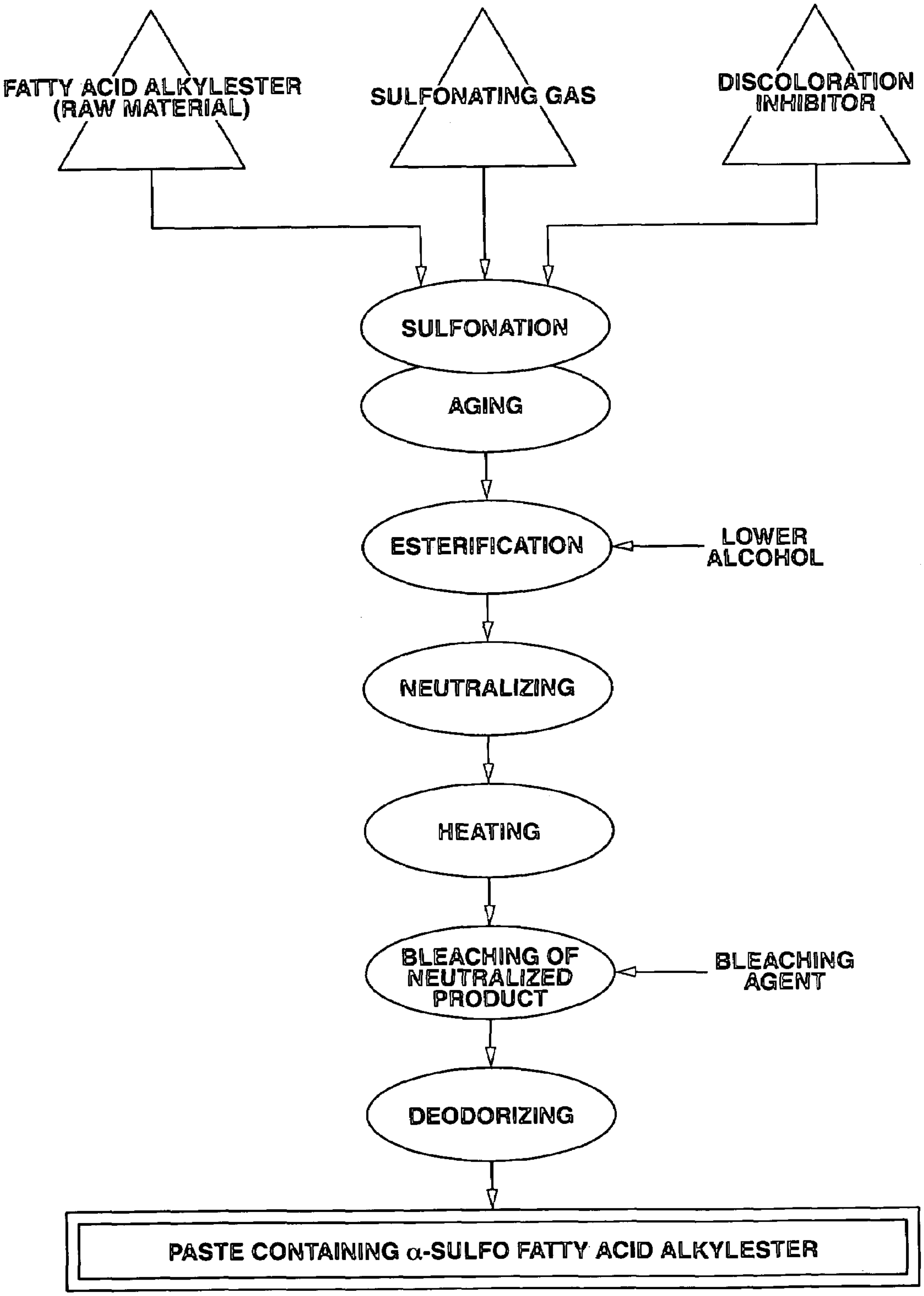
FIG. 1 is a flowchart showing an example of the process for producing a paste containing α-sulfofatty acid alkylester salt according to the present invention.
Figure 2:
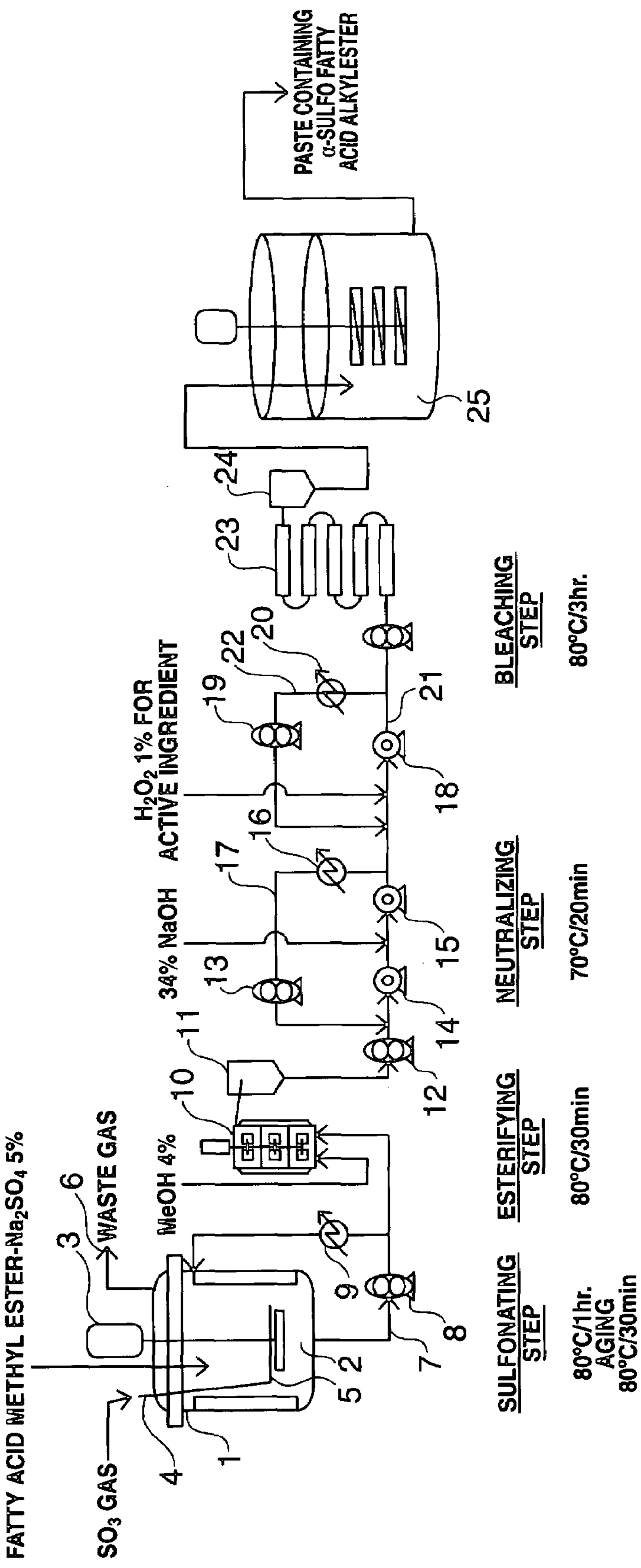
FIG. 2 is a schematic diagram showing an example of an apparatus used for the process according to the present invention.
Figure 3:
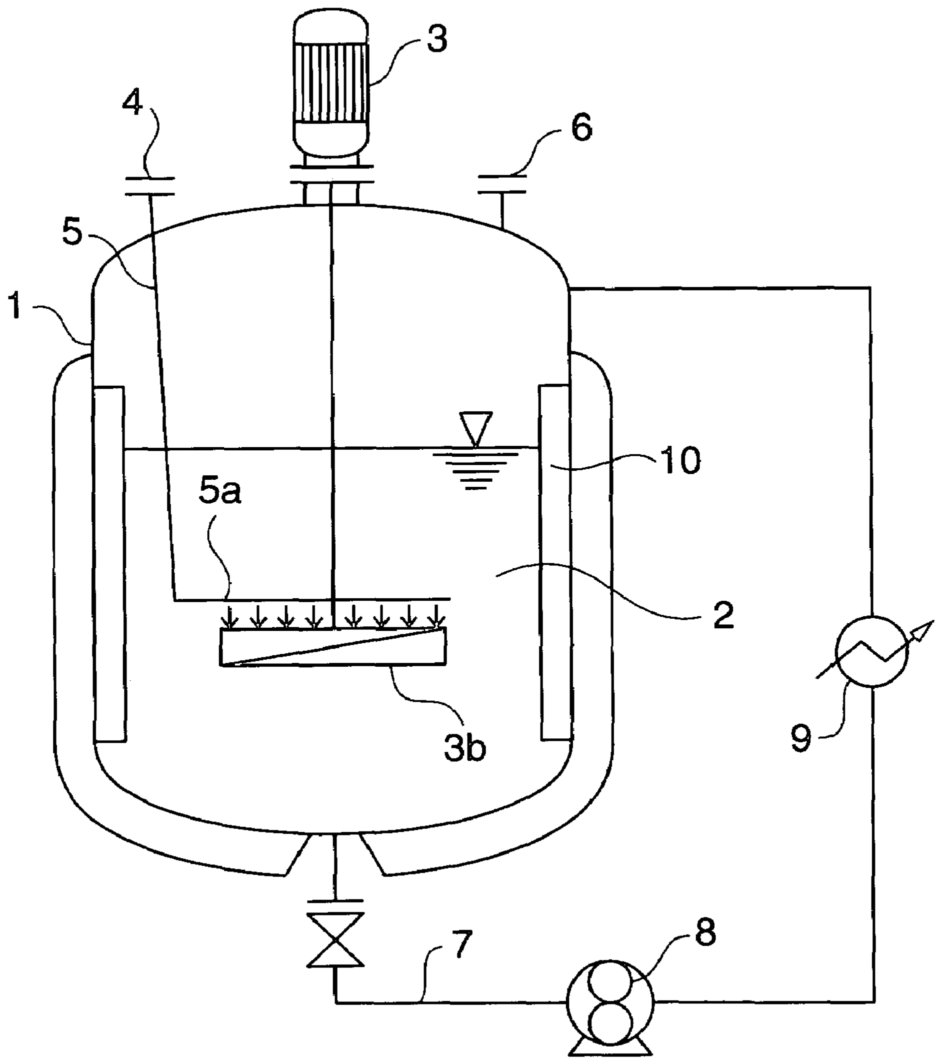
FIG. 3 is a schematic diagram showing an example of a sulfonating reactor.

FIG. 1 is a flowchart showing an example of the process for producing a paste containing α-sulfo fatty acid alkylester salt according to the present invention. FIG. 2 is a schematic diagram showing an example of the apparatus used for production. FIG. 3 is a schematic diagram showing an example of the sulfonating reactor. The apparatus shown in FIG. 2 uses the following materials for each reaction under the condition specified. Fatty acid methylester as a fatty acid alkylester (raw material). $SO_3$ gas diluted with dehumidified air or nitrogen gas as a sulfonating gas. $Na_2SO_4$ (sodium sulfate) as a discoloration inhibitor. Methanol as a lower alcohol. NaOH aqueous solution as an alkaline aqueous solution. $H_2O_2$ (hydrogen peroxide) as a bleaching agent. In FIG. 2, "%" means "wt %". Thus, FIG. 2 should be interpreted to mean that $Na_2SO_4$ is used as much as 5 wt % for the raw material, methanol is used as much as 4 wt % for sulfonic acid, and hydrogen peroxide is used as much as 1.0 wt % (on net basis) for the active ingredient (α-sulfo fatty acid alkylester salt).

A description is given below with reference to FIGS. 2 and 3 about the process for production of a paste containing α-sulfo fatty acid alkylester salt.

First, a reaction vessel 1 of mixing type for batch process (equipped with a stirrer) is charged with a fatty acid alkylester (as the raw material) and a discoloration inhibitor.

The fatty acid alkylester as the raw material is not specifically restricted; it includes animal fat and oil (such as beef tallow, fish oil, and lanolin), vegetable oil (such as coconut oil, palm oil, and soybean oil), and synthetic fatty acid alkylester derived from α-olefin by the oxo process. Their typical examples are listed below.

Methyl laurate, ethyl laurate, and propyl laurate. Methyl myristate, ethyl myristate, and propyl myristate. Methyl palmitate, ethyl palmitate, and propyl palmitate. Methyl stearate, ethyl stearate, and propyl stearate. Hardened tallow fatty acid methyl, ethyl, and propyl. Hardened fish oil fatty acid methyl, ethyl, and propyl. Palm oil fatty acid methyl, ethyl, and propyl. Palm oil fatty acid methyl, ethyl, and propyl. Palm kernel oil fatty acid methyl, ethyl, and propyl. They may be used alone or combination with one another.

According to the present invention, the fatty acid alkylester as the raw material should have an iodine value no larger than 1, preferably no larger than 0.5. The lower is the iodine value, the more desirable is the material from the standpoint of color and odor. The raw material with an iodine value in excess of 1 is good in color.

A desirable fatty acid alkylester in the present invention is one which is represented by the formula (1) below.

$$R^1CH_2COOR^2 \quad (1)$$

(wherein, $R^1$ is a $C_{6-24}$ straight or branched alkyl group or alkenyl group, and $R^2$ is a $C_{1-6}$ straight or branched alkyl group.)

It is desirable to carry out sulfonation in the presence of a discoloration inhibitor in order to obtain a light-colored α-sulfo fatty acid alkylester. The discoloration inhibitor is a monovalent metal salt of organic acid or inorganic sulfuric acid, with the latter being preferable. Organic salts are exemplified by sodium formate, potassium formate, and sodium acetate. Inorganic sulfates are exemplified by sodium sulfate, potassium sulfate, and lithium sulfate, which are monovalent metal salts in the form of anhydrous powder. Inorganic sulfates are inexpensive and yet highly effective in preventing discoloration. They are a common ingredient incorporated into detergent and hence they do not need to be removed from the α-sulfo fatty acid alkylester salt to be used for detergent.

The discoloration inhibitor should preferably have an average particle diameter no larger than 250 μm, especially preferably no larger than 100 μm. The reason for this is that the one having a small particle diameter disperses well into the liquid phase of the raw material owing to its large contact area, thereby enhancing its effect. (It should be noted that an inorganic sulfate hardly dissolves but mostly remains dispersed in the liquid phase of the raw material during reaction.) The discoloration inhibitor should preferably be added in an amount of 0-30 wt %, more preferably 0.5-20 wt %, further preferably 3-20 wt %, for the fatty acid alkylester as the raw material. It will not produce additional effect when used in an amount in excess of 30 wt %.

Although a reactor of vessel type (rector vessel 1) is used in figure, it is possible to use a reactor of any other type suitable for film reaction or tubular gas-liquid multiphase flow reaction. The process for sulfonation is not specifically restricted, but it includes film sulfonation and batch-type sulfonation. In the case of batch-type sulfonation, a reactor of vessel type is desirable because when the discoloration inhibitor is used at the time of sulfonation, it should preferably be uniformly dispersed into the raw material for contact with the sulfonating gas.

The raw material in the reactor vessel 1 is raised to a prescribed reaction temperature, with stirring by the stirrer 3. Thus, there is obtained the raw material liquid phase 2, which is composed of the raw material (in liquid form) and the discoloration inhibitor (in particulate form) dispersed therein. The reaction temperature is a temperature at which the fatty acid alkylester exhibits flowability. Usually, it is the melting point of the fatty acid alkylester, preferably 70° C. above the melting point.

A sulfonating gas is introduced into the raw material liquid phase 2 through the sulfonating gas inlet 4. The sulfonating gas is introduced through the gas sparger 5*a* connected to the gas inlet 5, and it is dispersed into the raw material liquid phase 2 by the stirrer 3. At the same time, the discoloration inhibitor (in particulate form) is uniformly dispersed into the raw material liquid phase 2.

The sulfonating gas should be introduced from the gas sparger 5*a* at a rate preferably no lower than 10 m/sec, more preferably 50-200 m/sec. Introducing with a flow rate lower than 10 m/sec will produce large bubbles.

The stirrer 3 should be run such that the tip speed of the end of the blade 3*b* is preferably 0.5-6.0 m/sec, more preferably 2.0-5.0 m/sec. Stirring at a tip speed lower than 0.5 m/sec will result in incomplete bubble dispersion and low reaction rates. This weakens the effect of preventing discoloration because the discoloration inhibitor is not dispersed completely. On the other hand, vigorous stirring at a tip speed in excess of 6.0 m/sec will not produce any additional effect but increases power consumption.

In this step, the sulfonating gas should usually be introduced over a period of 10-180 minutes for production efficiency. This period may be extended over 180 minutes if prevention of discoloration is more important than production efficiency. Extending the period for slow contact between the sulfonating gas and the raw material liquid phase 2 prevents the α-sulfo fatty acid alkylester from discoloration.

The sulfonating gas may be $SO_3$ gas or fuming sulfuric gas, with the former being preferable. The $SO_3$ gas should preferably be used after dilution to 1-40 vol % with dehumidified air or nitrogen (or any other inert gas). Excessively diluted $SO_3$ gas (lower than 1 vol %), which means a volume of the sulfonating gas is large, will need a large reactor to hold it. The large reactor may causes inconvenient. On the other hand, insufficiently diluted $SO_3$ gas (higher than 40 vol %) will bring about vigorous reactions, giving rise to more by-products and causing discoloration to sulfonated products such as α-sulfo fatty acid alkylester. Especially, in the case where the sulfonated product is α-sulfo fatty acid alkylester, dilution to 1-30 vol % is desirable to prevent its discoloration.

The molar amount of $SO_3$ gas used for reaction should suitably be 1.0-2.0 times, preferably 1.0-1.7 times, more preferably 1.05-1.5 times, the amount of the raw material. The molar amount less than 1.0 times may be not enough for complete sulfonation. The molar amount in excess of 2.0 times causes vigorous sulfonation, which results in by-products and discoloration.

After introduction of sulfonating gas into the raw material liquid phase 2 as mentioned above, the reaction vessel 1 should be kept at a prescribed temperature for aging. This aging temperature should preferably be 70-100° C. Aging below 70° C. does not proceed rapidly, and aging above 100° C. causes discoloration.

Aging should preferably last for 1-120 minutes. During aging, the stirrer should be run so that the stirring blades 3*b* keep the prescribed tip speed as mentioned above. This helps the discoloration inhibitor to uniformly disperse during aging. In this example in FIG. 2, sulfonation is carried out at 80° C. for 1 hour and aging is carried out at 80° C. for 30 minutes.

Then, the sulfonating step is followed by esterification with lower alcohol. This step is intended to suppress by-products and to improve the purity of the α-sulfo fatty acid alkylester salt, and hence it may be omitted if the above-mentioned sulfonation and aging give highly pure α-sulfo fatty acid alkylester (with little $SO_3$ di-adduct in the reaction solution). However, this step should preferably be carried out.

The lower alcohol for esterification should preferably be one which has the same carbon number (1 to 6) as the alcohol residue in the fatty acid alkylester as the raw material, although it is not specifically restricted. It should be used suitably in a molar amount 0.5-10 times, preferably 0.8-5.0 times, the $SO_3$ di-adduct in the reaction solution. A molar amount less than 0.5 times may be not enough for complete esterification. A molar amount more than 10 times may be not produce any additional effect but needs recovery of excess lower alcohol. The reaction temperature should suitably be 50-100° C., preferably 50-90° C., and the reaction time should be 5-120 minutes. In this FIG. 2 example, they are 80° C. and 30 minutes.

After esterification, the sulfonated product is discharged from the esterification reaction vessel 10 and then supplied to the neutralizing line 17 by the esterified acid supply pump 12, so that it is neutralized with an alkaline aqueous solution. Neutralization should be carried out so as to give a neutralized product in which the concentration of the active ingredient (purity content of α-sulfo fatty acid alkylester salt) is preferably 10-80 wt %, more preferably 60-80 wt %, further preferably 62-75 wt %. It is 70 wt % in the process under the condition shown in FIG. 2. In the range of 10 wt % to 60 wt %, the neutralized product increases in viscosity in proportion to concentrations, with productivity being poor at low concentrations. In the range of 60 wt % to 80 wt %, the neutralized product has a low viscosity adequate for good handling and productivity.

The alkaline aqueous solution should be any aqueous solution of alkali metal hydroxide, alkaline earth metal hydroxide, ammonia, or ethanolamine. The concentration of the alkaline aqueous solution should preferably be no higher than 50 wt %, more preferably 15-50 wt %. If the concentration is lower than 15 wt %, the resulting neutralized product will not contain the active ingredient (α-sulfo fatty acid alkylester salt) in the desired concentration (from 60 wt % to 80 wt %). In this FIG. 2 example, the concentration of the alkaline solution is 34 wt %. In the present invention, preliminary neutralized product should suitably be mixed with the sulfonated product by premixer 14. The neutralized product (or preliminary neutralized product) to be added to the sulfonated product should suitably be 5-25 times, preferably 10-20 times, the total amount (in weight) of the sulfonated product and the alkaline aqueous solution added thereto. An amount less than 5 times may be not enough to suppress by-products. An amount more than 25 times may be unfavorable to productivity. In this example, the amount is 20 times.

The neutralized product decreases in viscosity due to residual lower alcohol in the neutralizing step as mentioned above. This prevents α-sulfo fatty acid dialkali salt (as by-product) from occurring due to partial contact between the sulfonated product and the locally concentrated alkaline aqueous solution that takes place in the initial stage of reaction. In addition, the presence of lower alcohol suppresses the occurrence of by-products. Incidentally, the temperature of neutralization should suitably be 30-140° C., preferably 50-120° C., more preferably 50-100° C., and the duration of neutralization should preferably be 10-60 minutes. Also, the neutralizing step should preferably be carried out such that the mixture of the sulfonated product and the alkaline aqueous solution is acid or weakly alkaline (pH 4-9). If the mixture is strongly alkaline, the ester linkage is likely to break. The neutralizing step in the present invention may also be accomplished by reacting the sulfonic acid with a solid metal carbonate or hydrogen carbonate instead of using the alkaline aqueous solution. Neutralization with concentrated soda ash (as a solid metal carbonate) is desirable because of its lower price than other bases. In addition, neutralization with the solid metal carbonate yields a reaction mixture containing a less amount of water, preventing it from becoming strongly alkaline. A metal carbonate has an advantage over a metal hydroxide in generating a less amount of heat of neutralization. Examples of the metal carbonate or hydrogen carbonate include sodium carbonate, potassium carbonate, ammonium carbonate, sodium hydrogencarbonate, potassium hydrogencarbonate, and ammonium hydrogencarbonate, in anhydrous or hydrate form. They may be used alone or in combination with one another. In this FIG. 2 example, the neutralizing step is carried out at 70° C. for 20 minutes.

The neutralizing step should preferably be preceded or followed by a step of improving (or bleaching) the color of the α-sulfo fatty acid alkylester salt with a bleaching agent. The bleaching step should preferably be placed after the neutralizing step.

Examples of the bleaching agent include hydrogen peroxide and hypochlorite in the form of aqueous solution in any concentration. The bleaching agent should suitably be used in an amount of 0.1-10 wt %, preferably 0.1-5 wt % (on net basis), for the amount of the active ingredient(α-sulfo fatty acid alkylester salt). In this FIG. 2 example, the bleaching agent is used in an amount of 1.0 wt % (on net basis) for the amount of the active ingredient. In this FIG. 2 example, the bleaching step is intended to bleach the neutralized product. The advantage of bleaching in this manner over the conventional bleaching process, which is carried out at the same time as the sulfonated product is esterified, is that bleaching keeps the neutralized product stable without side reactions (due to esterification) and achieves its object with a less amount of bleaching agent than is required in the conventional process. In this FIG. 2 example, the amount of hydrogen peroxide is 1.0 wt % (on net basis) for the amount of the active ingredient. The preliminary bleached product (the neutralized product which has been mixed with the bleaching agent) should preferably be mixed in an amount of 5-30 times (in weight) the neutralized product which may be not yet bleached. An amount less than 5 times does not produce the effect of suppressing by-products. An amount more than 30 times will adversely affect productivity.

The bleaching temperature should suitably be 50-140° C., preferably 60-120° C., for hydrogen peroxide, and 30-80° C. for hypochlorite. The bleaching agent should be supplied such that the total reaction time in the mixing line 21 and the bleaching line 23 is about 30-360 minutes. In this FIG. 2 example, the bleaching temperature is 80° C. and the reaction time is 3 hours. Incidentally, bleaching should preferably be carried out at pH 4-9.

A heating step may be placed between the neutralizing step and the bleaching step, although it is not shown in FIG. 2. This heating step will improve the color of the finished powder. To this end, the neutralized product should suitably be heated 80° C. or above, preferably at 80-170° C., suitably for 0.5 hours to 7 days, preferably 1 hour to 5 days, more preferably 2-24 hours.

(2) The first aging step for aging the resulting paste

The paste containing α-sulfo fatty acid alkylester salt is transferred to the bleaching tank 25, in which it undergoes the first aging step for color improvement. Aging is defined as the process of keeping the paste at a prescribed temperature for a prescribed period of time. The aging temperature should suitably be 60-90° C., preferably 70-80° C. The aging period should suitably be 1-48 hours, preferably 2-24 hours, more preferably 2-12 hours. Aging at a temperature below 60° C. or aging for a period less than 1 hour will not improve the color of the paste. Aging at a temperature above 90° C. or aging for a period more than 48 hours will hydrolyze the α-sulfo fatty acid alkylester salt. The foregoing step gives the paste containing α-sulfo fatty acid alkylester salt which is used as the raw material for powder, flakes, or pellets.

(3) The step of making the aged paste into flakes or pellets containing equal to or less than 10 wt % of water, or the step of making the aged paste into flakes or pellets containing equal to or less than 10 wt % of water and then crushing the resulting flakes or pellets into powder having an average particle diameter of 100-1500 μm.

The paste containing α-sulfo fatty acid alkylester salt which has been obtained by the above-mentioned step is subsequently concentrated to give flakes or pellets containing equal to or less than 10 wt % of water. The apparatus and method for concentration are not specifically restricted. Some examples are: open-type mixer (vertical kneader and ribbon mixer), for mixing and concentrating at 70-120° C. for 1-15 hours; film evaporator ("Evaolator" from Sakura Seisakusho, "Exeva" from Shinko Pantec, "Kontro" from Hitachi Ltd.) and SVC concentrator (from Sakuma Seisakusho) for flash concentration by vacuum evaporation in an evaporator at a reduced pressure; and drum-type concentrator (CD drier from Nishimura Tekkousyo), self-cleaning-type concentrator (SC processor from Kurimoto), and custom drier (from Okawara MFG).

In the present invention, it is desirable to use the film evaporator and flash concentrator from the standpoint of productivity.

The film evaporator should be run in the following manner. First, the paste containing α-sulfo fatty acid alkylester salt is fed into a cylindrical casing equipped with stirring blades or puddles. The paste is spread over the heat-conducting surface by the centrifugal force of the stirring blades. Water and low-boiling components evaporate by heat (from the heating medium circulating through the wall jacket) and stirring heat. The amount of water to be evaporated may be controlled by adjusting the rate at which the paste is added, the revolution and tip speed of the stirring blades, the clearance between the wall surface and the blade ends, the degree of vacuum in the concentrator, and the jacket temperature. The tip speed of the stirring blades should preferably be 5-30 m/s, more preferably 5-25 m/s. Stirring at a lower speed than 5 m/s will not spread the paste completely over the wall surface and perform smooth liquid exchange. On the other hand, stirring at a higher speed than 30 m/s will produce frictional heat, thereby raising the temperature of the concentrated product and increasing mechanical load on the concentrator.

The clearance between the wall surface and the blade end should preferably be 0.5-5 mm, more preferably 1-4 mm, and most desirably 1-3 mm. A clearance smaller than 0.5 mm will prevent stable operation in full-size machine for mass production. A clearance larger than 5 mm will prevent the spreading and liquid exchange of the concentrated paste.

The degree of vacuum in the concentrator should preferably be 0.0040 MPa to the atmospheric pressure, more preferably 0.0040 MPa to 0.067 MPa. At a pressure lower than 0.0040 MPa, it may be difficult to discharge the concentrated product (with a high viscosity) from the concentrator. On the other hand, at a pressure higher than the atmospheric pressure, water vapor may become saturated in the film evaporator, thereby decreasing the efficiency of evaporation.

The size of the concentrator is not specifically restricted. The cylindrical casing may be 0.2-1.0 mm in inside diameter and 0.5-10 m long (heat conducting part), with the heat conducting area of 0.2-126 $m^2$. The residence time on the heat-conducting surface in the concentrator should preferably be 0.15 seconds to 10 minutes, more preferably 0.3 seconds to 10 minutes.

The flash concentration is accomplished by injecting the heated paste containing α-sulfo fatty acid alkylester salt into a flash evaporator. Thus, there is obtained a concentrated and dried paste containing α-sulfo fatty acid alkylester salt. Flash evaporation brings about evaporation immediately as soon as a liquid is fed into a flash evaporator under reduced pressure from an atmosphere at a high temperature and pressure. The pressure in the flash evaporator should preferably be 0.0010 MPa to atmospheric pressure. The water content in the concentrated product may be controlled by regulating the pressure in the flash evaporator, the jacket temperature of the heater, and the flow rate of the paste.

The concentrated paste, which contains equal to or less than 10 wt % of water, is usually a viscous paste which is as hot as above 70° C. immediately after the step of concentration. At such a high temperature, it is too sticky to be crushed readily by a crusher.

Therefore, in the present invention, the concentrated paste should preferably be cooled prior to the subsequent steps for crushing. In this case, the cooling may preferably be simultaneously with or after flaking or pelletizing. By these steps, the concentrated paste can be less-sticky, so enable to be processed sufficiently. The temperature after cooling is preferably 20-70° C., more preferably 20-60° C.

The cooling apparatus and method are not specifically restricted. Some examples are: Air-cooler or belt-type vacuum cooler ("Belmax" from Okawara MFG) and steel-belt cooler (from Sandvik). Cooling and flaking can be conducted at the same time by using a drum cooler, such as "Drum Flaker" from Kusunoki Kikai Seisakusho and "Double Drum Dryer" from Kansorn. As mentioned above, it is possible to obtain the concentrated paste containing α-sulfo fatty acid alkylester salt in the form of flakes simultaneously with cooling, or it is possible to make the concentrated paste into pellets and then cool them.

The thus obtained flakes or pellets may be crushed into a powder having a desired average particle diameter by using a crushing-granulator, if necessary. The crushing-granulator is not specifically restricted. Desirable ones are listed below.

A crushing-granulator equipped with a rotor and sieve inside, preferably an impact crusher, such as hammer mill, atomizer, and pulverizer, and a cutting-shearing crusher, such as cutter mill and feather mill. Their typical examples include Fitz Mill (from Hosokawamicron), Speed Mill (from Okada Seiko), Power Mill (from Dalton), Atomizer (from Fuji Powdal), Pulverizer (from Hosokawamicron), and Comminutor (from Fuji Powdal).

The preferred crushes is one which crushes the concentrated paste containing α-sulfo fatty acid alkylester salt and then discharges crushed particles through the screen having a prescribed opening. In general, it is desirable to introduce cold air into the crusher in order to prevent the crushed product from softening (due to crushing heat) and sticking to the crusher. The temperature of the cold air should preferably be 5-30° C., more preferably 5-25° C. The cold air should preferably be one which has been dehumidified or diluted with nitrogen. In addition, it is desirable to add grinding aid for crushing, at the time of grinding. The grinding aid reduces the crushing power, gives the desired particle size, and improves the powder properties, when added in a small amount into the crusher. Concretely, an inorganic powder, which mentioned later, is useful.

The screen is not specifically restricted; it may be of wire net type, herringbone type, or punched metal type. The last one is desirable in view of the screen strength and the powder shape.

The crusher may be of hammer type or cutter type mentioned above; the second type is desirable from the standpoint of avoiding the occurrence of fine powder due to impact crushing. The cutter blades should be coated with stellite or tungsten carbide so that they will not wear out after prolonged operation.

The average particle diameter of the crushed product (powder) should be 100-1500 μm, preferably 200-800 μm. Powder with an excessively large particle diameter may slow to dissolve during washing, which leads to low detergency and sticking to clothes. On the other hand, powder with an excessively small particle diameter causes dusting (with fine powder), decreases the crushing yields, and aggravates the flowability. The bulk density of the powder should generally be 0.2-1.4 g/$cm^3$, preferably 0.3-1.0 g/$cm^3$, more preferably 0.4-0.8 g/$cm^3$.

(4) The second aging step for aging the powder, flakes, or pellets

The powder, flakes, or pellets containing α-sulfo fatty acid alkylester salt in high concentrations, which have been produced by the foregoing steps, subsequently undergo the second aging step.

Aging is defined, in the same way as mentioned above, as the process of keeping the product at a prescribed temperature for a prescribed period of time. The second aging step in the present invention is accomplished by allowing the powder, flakes, or pellets to stand. Aging in this manner improves their properties such that they do not cake or deteriorate in flowability during storage or after they have been made into a final product. The aging temperature should preferably be 5-60° C., preferably 10-45° C. Aging at a temperature lower than 5° C. will not crystallize the α-sulfo fatty acid alkylester salt. Aging at a temperature higher than 60° C. will deteriorate the properties, which causes caking. The duration of aging should preferably be equal to or longer than 10 minutes, more preferably equal to or longer than 30 minutes, more preferably longer than 60 minutes. Duration shorter than 10 minutes is not enough to crystallize the α-sulfo fatty acid alkylester salt, and this leads to caking during storage in a large storage tank, such as silo.

The thus obtained powder, flakes, or pellets should be mixed with an inorganic powder for improvement of their properties. The inorganic powder should have an average particle diameter of 0.1-100 μm, preferably 0.5-50 μm, more preferably 0.5-30 μm. The amount of the inorganic powder should preferably be 1-40 wt %, more preferably 1-30 wt %, further preferably 1-20 wt %. With an average particle diameter smaller than 0.1 μm, the inorganic powder may cause dusting. With an average particle diameter larger than 100 μm, the inorganic powder may make the powder mixture inhomogeneous due to separation during storage. With an amount less than 1 wt %, the inorganic powder can not avoid that the powder, flakes or pellets to stick together for coalescence. With an amount more than 40 wt %, the inorganic powder adversely affects the flowability of the powder mixture. The inorganic powder may be mixed with the flakes or pellets as such or during or after their crushing. The mixing apparatus is not specifically restricted so long as it is capable of dry mixing. Its typical examples include a horizontal cylindrical mixer, V-type mixer, and agitation granulator.

The inorganic powder may be either a water-soluble one or a water-insoluble one. More than one kind of inorganic powder may be suitably used in combination with one another. The inorganic powder is not specifically restricted so long as it has the above-mentioned average particle diameter. It includes, for example, stearate, aluminosilicate (such as A type zeolite), sodium carbonate, calcium carbonate, magnesium carbonate, alkaline earth metal carbonate, amorphous silica, white carbon (silica), sodium silicate, calcium silicate, magnesium silicate and other silicates, clay mineral (such as talc and bentonite), silicon dioxide, titanium dioxide, pulverized sodium carbonate, sodium sulfate, potassium sulfate, sodium tripolyphosphate, and sodium citrate.

The flakes or pellets containing the α-sulfo fatty acid alkylester salt which have been produced by the process of the present invention may be used in the crushed form after crystallization has proceeded in the α-sulfo fatty acid alkylester salt. In this case, they may be mixed or coated with one or more than one kind of the above-mentioned inorganic powder having an average particle diameter of 0.1-100 μm, preferably 0.5-50 μm, more preferably 0.5-30 μm, as an agent to prevent them from sticking to the crusher or to improve the power properties.

If the thus obtained powder causes dusting, a small amount of nonionic surfactant may be sprayed thereto. By the spraying, it is possible to prevent the scattering of fine powder, thus dusting is reduced.

Process for Production of Granular Detergent

The present invention also provides a process for producing a granular detergent from the powder, flakes, or pellets produced by the above-mentioned process, by mixing with or granulating in conjunction with detergent components by any one method selected from powder mixing, kneading-crushing, and stirring granulation.

The detergent components are those materials which are incorporated into the powder, flakes, or pellets produced by the above-mentioned process. They include cleaning agents, bleaching agents, and any other agents to improve manufacturability and powder properties. They may be selected without specific restrictions from those which are commonly used for detergents. The detergent components that can be used for the granular detergent of the present invention include anionic surfactants, nonionic surfactants, cationic surfactants, amphoteric surfactants, chelating agents (zeolites and organic builders), neutral inorganic builders, alkaline inorganic builders, anti-redeposition agents, viscosity controlling agents, softeners, reducing agents, bleaching agent, bleach activating agents, fluorescent whitening agents, perfumes, enzymes, pigment, surface modifiers, anti-foaming agents, antioxidants, and water.

The detergent components contained in the detergent are not specifically restricted in their form; they may be used as such or in the form of detergent particles. The detergent particles are not specifically restricted so long as they contain any component which helps the above-mentioned detergent components to produce their effect. Those which contain both alkaline builder and chelating agent are desirable. No specific restrictions are imposed on the mixing ratio in the detergent of the detergent components to the powder, flakes, or pellets containing the α-sulfo fatty acid alkylester salt in high concentrations.

The granular detergent is obtained from the powder, flakes, or pellets containing the α-sulfo fatty acid alkylester salt in high concentrations and the detergent components by any one method selected from powder mixing, kneading-crushing, and stirring granulation.

The powder mixing involves mixing the powder containing the α-sulfo fatty acid alkylester salt in high concentrations with detergent components, particularly granular detergent components, in an apparatus capable of powder mixing. Mixing is preferred performed at 5-60° C., preferably 10-50° C., for 0.5 seconds or more, more preferably 5 seconds or more, most desirably 30 seconds or more. The upper limit of the mixing time is not specifically restricted. The apparatus used for powder mixing is not specifically restricted; horizontal cylindrical mixers, V-type mixers, and agitation granulators are desirable.

The kneading-crushing consists of two stages of kneading and crushing. In the kneading stage, the powder, flakes, or pellets containing the α-sulfo fatty acid alkylester salt in high concentrations are kneaded with the detergent components by using a continuous kneader (KRC kneader from Kurimoto Tekkosho) or a batch-type kneader (vertical kneader from Dalton) to give a lumpy product. In the crushing stage, the lumpy product is crushed by a crusher (Fitz Mill from Hosokawamicron or Speed Mill from Okada Seiko) to give detergent particles. During crushing, the crusher may be supplied with fine inorganic particles (such as zeolite, sodium carbonate, and white carbon) so that the material being crushed will not stick to the crusher. It is also desirable to feed cold air as mentioned above.

The stirring granulation forms granules from the powder or flakes containing the α-sulfo fatty acid alkylester salt in high concentrations and the detergent components by using a stirring-granulator, such as Loedige mixer (from Matsubo), Shuggy Mixer (from Powlex), High Speed Mixer (from Fukae Kogyo), and Plough-Shear Mixer (from Pacific Machinery & Engineering). If necessary, the resulting granules are classified by crushing and sieving.

According to an alternative process, the powder, flakes, or pellets produced by the above-mentioned process are mixed with the detergent components and water to give a slurry containing 20-50 wt % of water, and the resulting slurry is made into a granular detergent by spray drying. Upon mixing, the detergent components may be dispersed or dissolved in water. In this case, the mixing ratio (in weight) in the granular detergent of the powder, flakes, or pellets containing the α-sulfo fatty acid alkylester salt to the detergent components should preferably be from 70:30 to 2:98, more preferably from 30:70 to 5:95, further preferably from 20:80 to 5:95.

The detergent components used in this case may be the same ones as mentioned above. The order in which they are added is not specifically restricted. If they contain LAS—H, α-sulfo fatty acid alkylester salt, and alkali builder or zeolite, it is desirable to add LAS—H to the slurry (which has been neutralized), and then add alkali builder or zeolite, and finally add the α-sulfo fatty acid alkylester salt. The water content in the slurry should preferably be 20-50 wt %, more preferably 35-45 wt %. The thus obtained detergent slurry should be kept suitably at 50-90° C., preferably at 55-80° C.

This slurry is sprayed into a drying tower by using an atomizer of any type (including pressure nozzle type, air atomizing nozzle type, and rotary disk type). An atomizer of pressure nozzle type is desirable because the dried powder should suitably have an average particle diameter of 100-700 μm, preferably 150-500 μm. The drying tower is supplied with a hot gas at desirable 150-350° C., preferably 200-280° C., so that the atomized slurry is dried to give spray-dried particles. If the resulting spray-dried powder has an excessively high temperature, it will be poor in flowability with sticking. In order to avoid such troubles, the spray-dried product may be supplied with cold air or inorganic fine particles.

The present invention further provides a process for producing a granular detergent by mixing or granulating the granular detergent produced by the process mentioned above with detergent components by any one method selected from powder mixing, kneading-crushing, and agitation granulation. The detergent components used in this process are the same ones as used for mixing or granulation with the powder produced by the above-mentioned process. Individual components may be the same or different.

The powder mixing, kneading-crushing, and agitation granulation are the same as mentioned above. The mixing ratio of the spray-dried particles to the detergent components should preferably be such that the α-sulfo fatty acid alkylester salt (on net basis) accounts for 4-90 wt %, preferably 5-54 wt %, more preferably 9-27 wt %.

Process for Production of Solid Detergent

According to the present invention, the powder, flakes, or pellets produced by the above-mentioned process may be mixed and kneaded with detergent components to give a solid detergent. If necessary, water may be added. The detergent components may be used in the form of granules. Such granules may be formed by any one method selected from spray-drying, kneading-crushing, or stirring granulation, or any other methods. Such granules may also be obtained from an acid precursor of anionic surfactant by neutralization with an alkaline powder.

A description is given below of the process for production of solid detergent. In the first stage, the powder, flakes, or pellets mentioned above are mixed with the detergent components (or granules formed from them) by using one mixer or two or more mixers arranged in series. The mixer is not specifically restricted. It may be any one of the apparatus used for powder mixing, kneading-crushing, and agitation granulation mentioned above. If necessary, the resulting kneaded mixture may be formed into pellets or strand by using an extrusion-granulator such as pelleter. The resulting mixture is stamped (by using a plodder) to give the solid detergent. The mixing ratio (by weight) in the solid detergent of the powder, flakes, or pellets containing the α-sulfo fatty acid alkylester salt to the detergent components should preferably be from 40:60 to 1:99, more preferably from 30:70 to 3:97, particularly from 20:80 to 3:97. Incidentally, the manufacturing process mentioned above is merely exemplary and it does not restrict the scope of the present invention.

The present invention provides a process for producing powder, flakes, or pellets containing an α-sulfo fatty acid alkylester salt in high concentrations, and a process for producing a granular detergent or solid detergent from said powder, flakes, or pellets. The α-sulfo fatty acid alkylester salt according to the present invention exhibits good powder properties (flowability and anti-caking under pressure) during storage and has improved color and reduced odor.

EXAMPLE

The invention will be described in more detail with reference to Examples and Comparative Examples, which are not intended to restrict the scope thereof. In the following example, "%" means wt % unless otherwise indicated.

The powder, flakes, pellets prepared and detergent in each example were measured for their properties by the following methods.

<Methods for Evaluation>

(1) Method for Testing the Tendency Toward Caking Under Pressure

A sample is placed in a cylindrical cell, measuring 50 mm in inside diameter and 50 mm in height. The sample is pressed under a load of 3 kg for 3 minutes at an ambient temperature of 45° C. The molded sample is removed from the cell and pressed under a load. The load required to break the molded sample is measured. The result is rated according to the following criterion.

<Criterion>

○: 0 to less than 3 kg

Δ: 3 to less than 4 kg

X: 4 kg or above (2) Method for Measuring Flowability of Powder (in Terms of Repose Angle θ)

A sample is dropped through a funnel about 20 cm above a board at an ambient temperature of 45° C. so that the sample piles up to form a cone on the board. The repose angle θ is calculated from the height and the radius of the base circle.

$$\theta: \tan\theta = \text{height}/\text{radius}$$

The result is rated according to the following criterion.

<Criterion>

○: $\theta \leqq 60°$

Δ: $60° < \theta \leqq 70°$

X: $70° < \theta$ (3) Method for Measuring the Color of Powder

A sample having a particle diameter of 500-710 μm is measured to determine the b value by using the Σ90 Color Measuring System (from Nippon Denshoku Industries). The larger is the b value, the more yellowish is the sample. It is possible to visually distinguish between two samples if their b value difference is greater than 1.0. The result is rated according to the following criterion.

<Criterion>

○: b value<13

Δ: 13≦b value<16

X: 16≦b value (4) Method for Measuring Odor

A sample is placed in a 30 mL glass container, 30 mm in diameter, so that the glass container is 80 vol % filled. The sample is stored at 50° C. for 2 weeks in the closed glass container. The glass container is opened and the presence or absence of unpleasant odor was determined by sensory test. The results are rated according to the following criterion.

<Criterion>

○: good

Δ: slightly bad

X: very bad

Examples 1 to 4

(1) Preparation of Paste Containing α-Sulfo Fatty Acid Alkylester Salt (Sulfonating Step)

Sulfonation was carried out by using the reactor shown in FIG. 3. This reactor is made of SUS 316L and has a capacity of 200 L. It is equipped with the cooling jacket and the stirrer 3, so that the reaction temperature is controlled by the circulating line 7. First, the reaction vessel 1 was charged with 92 kg of fatty acid methyl ester as the raw material. Sodium sulfate (in the form of fine powder) as a discoloration inhibitor was added with thorough stirring, in an amount of 5% for the fatty acid methyl ester. With stirring continued, 110-120 $m^3$ of $SO_3$ gas (as a sulfonating gas) diluted to 8 vol % with nitrogen gas was introduced at a constant flow rate through the ring sparger over 1 hour. The amount of $SO_3$ gas is equivalent to 1.2 times the amount (in mole) of the methyl ester as the raw material. During sulfonation, the reaction temperature was kept at 80° C. and the cooling medium was circulated at a flow rate of 80-100 L/min through the circulating line 7. After sulfonation, the reaction product was kept at 80° C. for 30 minutes.

(Esterifying Step)

Esterification was carried out by using the esterifying reaction vessel 10, which is of jacketed three-stage stirring type. For esterification, the reaction vessel was charged with methanol (as lower alcohol) at a rate of 3.5-5.5 kg/hr, which is equivalent to 3-4 wt % of the sulfonated product. The temperature of esterification was 80° C., and the aging period was 30 minutes.

(Neutralizing Step)

The sulfonated product was discharged from the esterification reaction vessel 10 and continuously supplied to the neutralizing line 17 at a flow rate of 130-135 kg/hr. Neutralization was accomplished by the method disclosed in Japanese Patent Laid-open No. 2001-64248. According to this method, an aqueous solution (25-35 wt %) of sodium hydroxide was fed at a constant rate of 50-60 kg/hr to the intermediate point between the premixer 14 and the neutralizing mixer 15. In other words, the sulfonated product was previously and thoroughly mixed with the preliminary neutralized product by the premixer 14, and the resulting mixture was mixed with the aqueous solution of sodium hydroxide for neutralization. The amount of the preliminary neutralized product circulating through the loop was 20 times the total amount of the sulfonated product and the alkaline aqueous solution added. The temperature of neutralization was kept at 70° C. by adjusting the water temperature of the heat exchanger 16 of the loop circuit. The residence time of the neutralized product was 20 minutes. Incidentally, the circulating loop is equipped with a pH control system (not shown in FIG. 2), which controls the supply of the aqueous solution of sodium hydroxide through a feedback controller. The pressure in the circulating loop was 4 $kg/cm^2$. The resulting neutralized product had pH 6.5.

(Bleaching Step)

The neutralized product was supplied to the bleaching agent mixing line 21 at a flow rate of 180-200 kg/hr. The bleaching agent mixing line 21 is adapted to circulating loop type, including the circulating line 22 equipped with the heat exchanger 20. The circulating line 22 is supplied with 35% hydrogen peroxide at a flow rate of 3.5-7.5 kg/hr (1-2% on net basis for the active ingredient (α-sulfo fatty acid alkylester salt)), so that it is thoroughly mixed therein with the neutralized product (preliminary bleached product) which has been mixed with the bleaching agent. The amount of loop circulation was 15 times the amount of the neutralized product newly added to the preliminary bleached product. The pressure in the circulating loop pipe was 4 $kg/cm^2$. The temperature of the circulating loop was adjusted to 80° C. by the heat exchanger 20, and the residence time in the circulating loop was 10 minutes. The bleached product was introduced into the bleaching line 23 of passage type, so that bleaching proceeded further. Incidentally, the bleaching line 23 is a jacketed double tube capable of temperature and pressure control. The flow of the bleaching agent mixture was a piston flow, and the pressure and temperature were adjusted to 4 $kg/cm^2$ and 80° C., respectively. The residence time was 180 minutes.

(2) The First Aging Step

The thus obtained paste containing α-sulfo fatty acid alkylester salt was transferred to the bleaching tank 25, in which it was aged under the condition shown in Table 1. The paste which had undergone the first aging step contained active ingredients (α-sulfo fatty acid alkylester salt) as shown in Table 1.

(3) Preparation of Powder or Flakes Containing α-Sulfo Fatty Acid Alkylester Salt (Concentrating Step)

The paste containing α-sulfo fatty acid alkylester salt which had been obtained by the above-mentioned step was fed into a vacuum film evaporator ("Exceva" from Shinko Pantec) at a flow rate of 5-90 kg/hr. This evaporator is equipped with stirring blades rotating at 1060 rpm, with the blade tip speed being about 11 m/sec. It has a heat-conducting area of 0.5 $m^2$, an inside diameter of 205 mm, and a clearance of 2-4 mm between the heat-conducting surface and the blade end. The paste was concentrated at 120-160° C. (the heating temperature of the inside wall) and at a degree of vacuum of 0.007-0.014 MPa. The temperature of the resulting concentrate was 70-100° C. The water content in the concentrate is shown in Table 1. The concentrate was cooled to 20-30° C. by using a drum flaker (from Kusunoki Kikai Seisakusho). Thus there were obtained flakes containing α-sulfo fatty acid alkylester salt in high concentrations.

(Crushing)

The flakes containing α-sulfo fatty acid alkylester salt in high concentrations, which were obtained in the concentrating step mentioned above, were fed into the Fitz Mill together with the inorganic powder (according to the formulation shown in Table 1), and dehumidified cold air (at 15° C., with a dew point of −5° C.). In Example 4, ordinary non-dehumidified cold air at 15° C. was used in place of dehumidified cold air. The flow rate of cold air was 6 $Nm^3$/min. Crushing was carried out at a throughput of 200 kg/hr. Two sets of Fitz mill arranged in series were used. Fitz Mill is Model DKA-3 of Hosokawamicron. It has a fist-stage sieve with an opening of 8 mmϕ and a second-stage sieve with an opening of 3.5 mmϕ, and a first-stage blade rotating at 4700 rpm and a second-stage blade rotating at 2820 rpm.

(4) The Second Aging Step

The crushed product (or powder) thus obtained underwent aging under the condition shown in Table 1. Thus there was obtained a powder containing α-sulfo fatty acid alkylester salt in high concentrations. The properties of the powder are shown in Table 1.

A description will be given later of the raw materials used.

Examples 5 and 6

Flakes containing α-sulfo fatty acid alkylester salt in high concentrations were prepared by the same steps (1)-(3) as in Example 1. Without mixing with the inorganic powder, the flakes were fed into two sets of Fitz mill arranged in series together with cold air diluted with nitrogen such that the oxygen content was 8%. Fitz Mill is Model DKA-3 of Hosokawamicron. It has a fist-stage screen with an opening of 8 mmϕ and a second-stage screen with an opening of 3.5 mmϕ, and a first-stage blade rotating at 4700 rpm and a second-stage blade rotating at 2820 rpm. The flow rate was 6 $Nm^3$/min. Crushing was carried out at a throughput of 150 kg/hr. The resulting crushed product (powder) underwent the second aging step under the condition shown in Table 1. Thus there was obtained a powder containing α-sulfo fatty acid alkylester salt. The properties of the powder are shown in Table 1.

In the following, "according to the method of the specific example" means that it should be a method according to the method described in the specific example and the materials, the amount and duration should conform to those mentioned in the table indicated.

Examples 7 to 9

Figure 4:
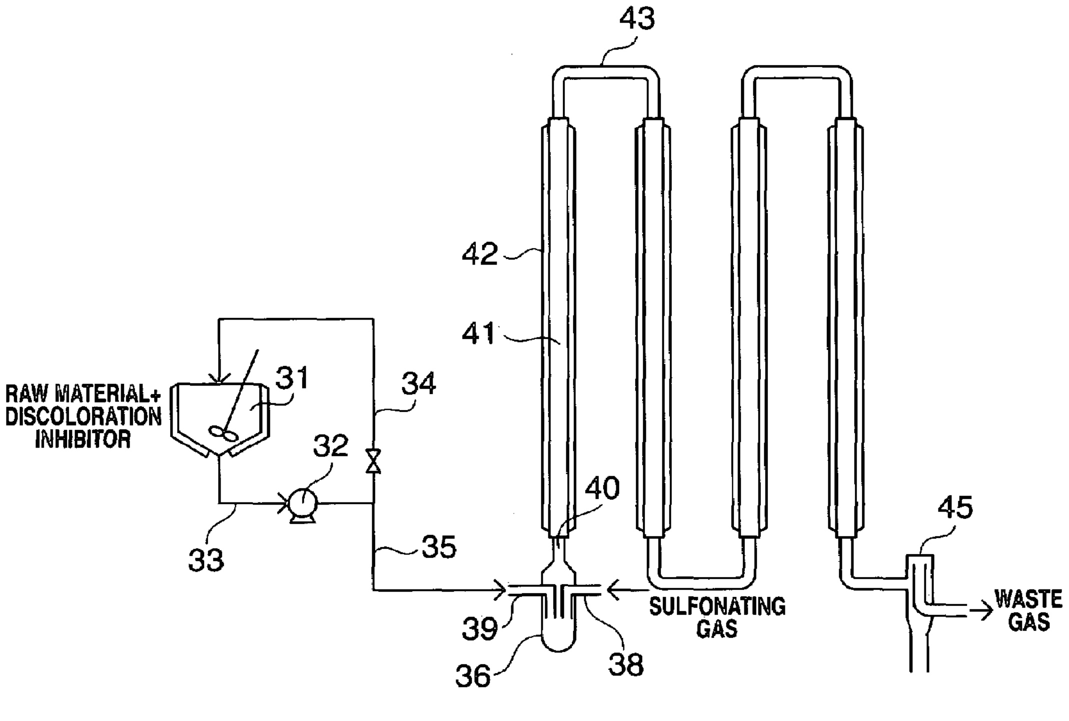
FIG. 4 is a schematic diagram showing an example of a reactor used for tubular gas-liquid multiphase flow reaction (pseudo-film reaction).

Sulfonation was carried out by using a gas-liquid mixed phase flow reactor (pseudo-film reactor) shown in FIG. 4 in place of the vessel-type reactor (the reaction vessel 1). The entry part 36 is a jacketed reaction mixer with a capacity of 100 mL. The jacketed reaction tube 41 is a stainless steel tube (SUS 316L), 13.8 mm in inside diameter and 2 m long. Four units of this tube are arranged in parallel. They are connected to one another through connecting tubes 43, 13.8 mm in inside diameter and 1 m long. The stirring vessel 31 was charged with fatty acid methyl ester (as the raw material) and sodium sulfate (as the discoloration inhibitor), 5 wt % for the raw material. The stirring vessel was heated to 50° C. and the sodium sulfate was uniformly dispersed into the liquid phase. The mixture was returned to the stirring vessel 31 through the circulating tube 34 by the pump 32 so as to prepare the thoroughly mixed solid-liquid phase. The flow rate in the discharging tube 33, the circulating tube 34, and the supply tube 35 was 0.7 m/sec, and the pressure in these tubes was 2 $kg/cm^2$.

The solid-liquid mixed phase was supplied to the entry part 36 from the raw material introducing tube 39 at a constant flow rate of 128 g/min. On the other hand, sulfonating gas (diluted to 8 vol % with nitrogen) was introduced quantitatively through the sulfonating gas introducing tube 38 at a flow rate of 0.3 $m^3$/min in the same way as in Example 1. The temperature of the entry part 36 was 80° C. and the temperature of the solid-liquid mixed phase in the reaction tube 41 was adjusted to 80° C. by controlling the cooling water in the jacket. The gas flow rate in the reaction tube 41 was 30 m/sec, the average thickness of the circular liquid film of the raw material was 0.3 mm, the flow rate was 5 cm/sec, and the residence time was 60 seconds. The sulfonated product was separated from the waste gas in the recovery part 45. The sulfonated product was introduced into the vessel-type reactor 1 shown in FIG. 2, and it was aged at a reaction temperature of 80° C. for 30 minutes. The esterifying step was followed by the same steps as in Example 1. Thus there was obtained a powder containing α-sulfo fatty acid alkylester salt. The properties of the powder are shown in Tables 1 and 2.

Examples 10 and 11

Flakes were prepared by the same steps (1)-(3) as in Example 1. In the case of Example 11, they were mixed with the inorganic powder according to the formulation shown in Table 2. Mixing was accomplished by using a horizontal cylindrical rotary drum (400 mm in diameter, 700 mm long, and having an Fr number of 0.14). The flakes (10 kg) and the inorganic powder in a prescribed amount shown in Table 2 were mixed for 2 minutes (In case of Example 10, they were not mixed with the inorganic powder.). Each resulting flake was aged under the condition shown in Table 2. Thus there were obtained the desired flakes containing α-sulfo fatty acid alkylester salt in high concentrations. The properties of the flakes are shown in Table 2.

Example 12

The flakes containing α-sulfo fatty acid alkylester salt which had been obtained in Example 10 were fed into the Fitz mill together with dehumidified cold air at 15° C. (with a dew point of −5° C.) and the inorganic powder as a grinding aid shown in Table 2. The flow rate was 6 $Nm^3$/min. Crushing was carried out at a throughput of 100 kg/hr. Thus there was obtained a powder containing α-sulfo fatty acid alkylester salt in high concentrations. Two sets of Fitz mill arranged in series were used. Fitz Mill is Model DKA-3 of Hosokawamicron. It has a fist-stage screen with an opening of 8 mmϕ and a second-stage screen with an opening of 3.5 mmϕ, and a first-stage blade rotating at 4700 rpm and a second-stage blade rotating at 2820 rpm. The properties of the powder are shown in Table 2.

Examples 13 and 14

The paste containing α-sulfo fatty acid alkylester salt which had been obtained by the steps (1) and (2) in Example 1 was fed into the vertical stirring mixer (from Dalton). The paste had its water evaporated by stirring at a jacket temperature of 90° C. for 8 hours. The resulting concentrate was made into pellets, measuring about 10 mm in diameter and 10-30 mm long on average, by using "Pelleter Double" (Model EXDFJS-60, from Fuji Paudal). In Example 14, the pellets were mixed with the inorganic powder in an amount specified in Table 2. Mixing was accomplished by using a horizontal cylindrical rotary drum (400 mm in diameter, 700 mm long, and having an Fr number of 0.14). The inorganic powder and 10 kg of pellets were fed into the drum; they were mixed together for 2 minutes; and then discharged. Thus, the mixture was obtained (In the case of Example 13, they were not mixed with the inorganic powde.). Subsequently, Each pellet was aged under the condition shown in Table 2. Thus there were obtained pellets containing α-sulfo fatty acid alkylester salt in high concentrations. The properties of the pellets are shown in Table 2.

Example 15

The pellets which had been obtained by the process mentioned in Example 13 were fed into the Fitz mill together with cold air (diluted with nitrogen such that the oxygen content was 8%) at 15° C. and the inorganic powder (as a grinding aid) in an amount shown in Table 2. The flow rate was 6 $Nm^3$/min, and the gas/solid ratio was 2.0 $m^3$/kg. Crushing was carried out at a throughput of 190 kg/hr to obtain the powder containing α-sulfo fatty acid alkylester salt in high concentrations. Two sets of Fitz Mill arranged in series were used. Fitz Mill is Model DKA-3 of Hosokawamicron. It has a fist-stage screen with an opening of 8 mmϕ and a second-stage screen with an opening of 3.5 mmϕ, and a first-stage blade rotating at 4700 rpm and a second-stage blade rotating at 2820 rpm. The properties of the resulting powder are shown in Table 2.

Examples 16 to 21

The procedure mentioned in Example 1 was repeated except that the inorganic powder shown in Tables 2 and 3 was used. Thus, there was obtained the desired powder containing α-sulfo fatty acid alkylester salt in high concentrations. The mixing of the inorganic powder was carried out by the procedure mentioned in Example 11. The properties of the resulting powder are shown in Tables 2 and 3.

Examples 22 to 24

The paste containing α-sulfo fatty acid alkylester salt which had been obtained by the steps (1) and (2) mentioned in Example 1 was fed into a film evaporator at a flow rate of 5-40 kg/hr. This evaporator is "Exceva" (from Shinko Pantec), which is equipped with stirring blades rotating at 1060 rpm, with the blade tip speed being about 11 m/sec. It has a heat-conducting area of 0.5 $m^2$, an inside diameter of 205 mm, and a clearance of 2-4 mm between the heat-conducting surface and the blade end. The paste was concentrated at 120-160° C. (the heating temperature of the inside wall) and atmospheric pressure. The temperature of the resulting concentrate was at 95° C. The water content in the concentrate is shown in Table 3. The concentrate was cooled to 20-30° C. by using a drum flaker (from Kusunoki Kikai Seisakusho). Thus there were obtained flakes containing α-sulfo fatty acid alkylester salt in high concentrations. In Examples 23 and 24, the flakes were crushed into powder by the procedure mentioned in Example 1. The resulting powder was aged under the condition shown in Table 3.

Comparative Example 1

The procedure mentioned in Example 1 was repeated to give a powder containing α-sulfo fatty acid alkylester salt in high concentrations, whose properties are shown in Table 4.

Comparative Example 2

The procedure mentioned in Example 1 was repeated to give a powder containing α-sulfo fatty acid alkylester salt in high concentrations, except that the resulting powder did not undergo aging. The properties of the resulting powder are shown in Table 4.

Comparative Example 3

The procedure mentioned in Example 1 was repeated to give flakes containing α-sulfo fatty acid alkylester salt in high concentrations, except that crushing was not performed and the resulting flakes did not undergo aging. The properties of the resulting flakes are shown in Table 4.

Comparative Example 4

The procedure mentioned in Example 14 was repeated to give pellets containing α-sulfo fatty acid alkylester salt in high concentrations, except that the resulting pellets did not undergo aging. The properties of the resulting pellets are shown in Table 4.

Comparative Example 5

The procedure mentioned in Example 1 was repeated to give a powder containing α-sulfo fatty acid alkylester salt in high concentrations, except that the paste containing α-sulfo fatty acid alkylester salt was concentrated without aging after it had been transferred to the bleaching tank. The properties of the resulting powder are shown in Table 4.

Incidentally, "Final product" in Tables means the powder, flakes, or pellets which have passed all the steps in Examples 1 to 31. Amount of inorganic powder and additive in Table 1-5 is amount of raw material described later.

TABLE 1

| | Example | | | | | | | |
|---|---|---|---|---|---|---|---|---|
| | 1 | 2 | 3 | 4 | 5 | 6 | 7 | 8 |
| Fatty acid methyl ester*[1] | A | A | B | C | B | A | A | B |
| Duration of aging of paste (hr) | 8 | 24 | 3 | 24 | 10 | 8 | 12 | 1 |
| Temperature of aging of paste (° C.) | 80 | 80 | 70 | 90 | 80 | 80 | 60 | 80 |
| Concentration of AI in paste (%) | 64.5 | 68.0 | 71.4 | 69.6 | 66.0 | 62.5 | 73.4 | 66.0 |
| Water content in concentrates (%) | 1.8 | 9.6 | 4.5 | 0.9 | 3.5 | 1.2 | 1.6 | 3.2 |
| Inorganic powder used | ZeO*[2] | ZeO | ZeO | ZeO | — | — | ZeO | ZeO |
| Average particle diameter of inorganic powder (μm) | 1 | 1 | 1 | 1 | — | — | 1 | 1 |
| Amount of inorganic powder (% based on final product) | 10 | 40 | 30 | 5 | — | — | 10 | 20 |
| Duration of aging of flakes (min) | — | — | — | — | — | — | — | — |
| Duration of aging of pellets (min) | — | — | — | — | — | — | — | — |
| Duration of aging of Powder (min) | 30 | 60 | 60 | 15 | 60 | 60 | 60 | 60 |
| Aging temperature (° C.) | 25 | 15 | 15 | 40 | 25 | 25 | 30 | 15 |
| Form of final product | Powder | Powder | Powder | Powder | Powder | Powder | Powder | Powder |
| Average particle diameter (μm) | 480 | 380 | 420 | 250 | 600 | 520 | 1000 | 730 |
| Bulk density (g/cm$^3$) | 0.61 | 0.43 | 0.49 | 0.65 | 0.62 | 0.60 | 0.63 | 0.58 |
| Tendency to caking under pressure | ○ | Δ | ○ | ○ | ○ | ○ | ○ | ○ |
| Angle of repose | ○ | Δ | Δ | ○ | ○ | ○ | ○ | Δ |
| Color of particulate product | ○ | ○ | ○ | Δ | ○ | ○ | ○ | ○ |
| Odor | ○ | ○ | ○ | ○ | ○ | ○ | ○ | ○ |

*[1]Fatty acid methyl ester: refer to table 25
*[2]Zeo: Zeolite

TABLE 2

| | Example | | | | | | | |
|---|---|---|---|---|---|---|---|---|
| | 9 | 10 | 11 | 12 | 13 | 14 | 15 | 16 |
| Fatty acid methyl ester | C | A | A | A | A | A | A | A |
| Duration of aging of paste (hr) | 18 | 12 | 12 | 12 | 12 | 12 | 12 | 12 |
| Temperature of aging of paste (° C.) | 80 | 80 | 80 | 80 | 80 | 80 | 80 | 80 |
| Concentration of AI in paste (%) | 64.5 | 64.5 | 64.5 | 64.5 | 64.5 | 64.5 | 64.5 | 64.5 |
| Water content in concentrates (%) | 5.0 | 1.8 | 1.8 | 1.8 | 2.1 | 2.1 | 2.1 | 1.8 |
| Inorganic powder used | ZeO | — | ZeO | ZeO | — | ZeO | ZeO | Tripoly*[3] |
| Average particle diameter of inorganic powder (μm) | 1 | — | 1 | 1 | — | 1 | 1 | 50 |
| Amount of inorganic powder (% based on final product) | 10 | — | 1 | 10 | — | 1 | 10 | 15 |
| Duration of aging of flakes (min) | — | 60 | 60 | 60 | — | — | — | — |
| Duration of aging of pellets (min) | — | — | — | — | 60 | 60 | 60 | — |
| Duration of aging of Powder (min) | 60 | — | — | — | — | — | — | 60 |
| Aging temperature (° C.) | 25 | 25 | 25 | 25 | 25 | 25 | 25 | 25 |
| Form of final product | Powder | Flakes | Flakes | Powder | Pellets | Pellets | Powder | Powder |
| Average particle diameter (μm) | 460 | — | — | 480 | — | — | 440 | 480 |
| Bulk density (g/cm$^3$) | 0.54 | — | — | 0.57 | — | — | 0.55 | 0.62 |
| Tendency to caking under pressure | ○ | ○ | ○ | ○ | ○ | ○ | ○ | ○ |
| Angle of repose | ○ | — | — | ○ | — | — | ○ | ○ |
| Color of particulate product | Δ | — | — | ○ | — | — | ○ | ○ |
| Odor | ○ | ○ | ○ | ○ | ○ | ○ | ○ | ○ |

*[3]Tripoly: Sodium tripolyphosphate

TABLE 3

| | Example | | | | | | | |
|---|---|---|---|---|---|---|---|---|
| | 17 | 18 | 19 | 20 | 21 | 22 | 23 | 24 |
| Fatty acid methyl ester | A | A | A | A | A | A | A | A |
| Duration of aging of paste (hr) | 12 | 12 | 12 | 12 | 12 | 12 | 12 | 12 |
| Temperature of aging of paste (° C.) | 80 | 80 | 80 | 80 | 80 | 80 | 80 | 80 |
| Concentration of AI in paste (%) | 64.5 | 64.5 | 64.5 | 64.5 | 64.5 | 64.5 | 64.5 | 64.5 |
| Water content in concentrates (%) | 1.8 | 1.8 | 1.8 | 1.8 | 1.8 | 2.3 | 2.3 | 2.3 |
| Inorganic powder used | Citric*[4] acid | Tripoly/ ZeO | Potassium*[5] sulfate/ ZeO | Sodium*[6] carbonate/ ZeO | Citric acid/ ZeO | — | — | ZeO |
| Average particle diameter of inorganic powder (μm) | 1 | 50/1 | 20/1 | 20/1 | 30/1 | — | — | 1 |
| Amount of inorganic powder (% based on final product) | 25 | 15/10 | 15/10 | 15/10 | 15/10 | — | — | 10 |
| Duration of aging of flakes (min) | — | — | — | — | — | 60 | — | — |
| Duration of aging of pellets (min) | — | — | — | — | — | — | — | — |
| Duration of aging of Powder (min) | 60 | 60 | 60 | 60 | 60 | — | 60 | 60 |
| Aging temperature (° C.) | 25 | 25 | 25 | 25 | 25 | 25 | 25 | 25 |
| Form of final product | Powder | Powder | Powder | Powder | Powder | Flakes | Powder | Powder |
| Average particle diameter (μm) | 520 | 480 | 430 | 460 | 480 | — | 580 | 540 |
| Bulk density ($g/cm^3$) | 0.60 | 0.53 | 0.54 | 0.53 | 0.55 | — | 0.61 | 0.58 |
| Tendency to caking under pressure | ○ | ○ | ○ | ○ | ○ | ○ | ○ | ○ |
| Angle of repose | ○ | ○ | Δ | Δ | ○ | — | ○ | ○ |
| Color of particulate product | ○ | ○ | ○ | ○ | ○ | — | ○ | ○ |
| Odor | ○ | ○ | ○ | ○ | ○ | ○ | ○ | ○ |

*[4]Citric acid: Pulverized sodium citrate
*[5]Potassium sulfate: Pulverized potassium sulfate
*[6]Sodium carbonate: Pulverized sodium carbonate [1]

TABLE 4

| | Comparative Example | | | | |
|---|---|---|---|---|---|
| | 1 | 2 | 3 | 4 | 5 |
| Fatty acid methyl ester | A | A | A | A | A |
| Duration of aging of paste (hr) | 8 | 8 | 8 | 8 | — |
| Temperature of aging of paste (° C.) | 80 | 80 | 80 | 80 | — |
| Concentration of AI in paste (%) | 70.1 | 70.1 | 70.1 | 70.1 | 70.1 |
| Water content in concentrates (%) | 15.3 | 8.0 | 8.0 | 8.0 | 4.5 |
| Inorganic powder used | ZeO | ZeO | ZeO | ZeO | ZeO |
| Average particle diameter of inorganic powder (μm) | 1 | 1 | 1 | 1 | 1 |
| Amount of inorganic powder (% based on final product) | 30 | 20 | 1 | 1 | 20 |
| Duration of aging of flakes (min) | — | — | — | — | — |
| Duration of aging of pellets (min) | — | — | — | — | — |
| Duration of aging of Powder (min) | 60 | — | — | — | 60 |
| Aging temperature (° C.) | 45 | — | — | — | 30 |
| Form of final product | Powder | Powder | Flakes | Pellets | Powder |
| Average particle diameter (μm) | 490 | 580 | — | — | 520 |

TABLE 4-continued

| | Comparative Example | | | | |
|---|---|---|---|---|---|
| | 1 | 2 | 3 | 4 | 5 |
| Bulk density ($g/cm^3$) | 0.61 | 0.66 | — | — | 0.60 |
| Tendency to caking under pressure | X | X | X | X | ○ |
| Angle of repose | Δ | ○ | — | — | ○ |
| Color of particulate product | ○ | ○ | — | — | X |
| Odor | ○ | ○ | ○ | ○ | X |

Examples 25 and 26

A mixture was obtained by uniform mixing in a stirring vessel from the paste containing α-sulfo fatty acid alkylester salt (which had been obtained by the steps (1) and (2) mentioned in Example 1) and additives according to the formulation shown in Table 5. The resulting mixture was processed by the steps (3) and (4) mentioned in Example 1 to give a powder containing α-sulfo fatty acid alkylester salt in high concentrations. The properties of the resulting powder are shown in Table 5.

Examples 27 and 28

A mixture was obtained by uniform mixing in a stirring vessel from the paste containing α-sulfo fatty acid alkylester salt (which had been obtained by the steps (1) and (2) mentioned in Example 1) and additives according to the formulation shown in Table 5. The resulting mixture was concentrated by the step mentioned in Example 13 and then processed (after crushing) by the procedure mentioned in Example 1 to give a powder containing α-sulfo fatty acid alkylester salt in high concentrations. The properties of the resulting powder are shown in Table 5.

Examples 29 to 31

A concentrate containing α-sulfo fatty acid alkylester salt was obtained by the steps (1) to (3) mentioned in Example 1. The resulting concentrate was at 70-100° C., and its water content is shown in Table 5. The resulting concentrate was introduced into KRC kneader (Model S-4, from Kurimoto Tekkosho) according to the formulation shown in Table 5. There was obtained a kneaded mixture at 60-90° C. The throughput of the kneader was 50 kg/hr. The kneaded mixture was fed into a pelleter (EXDFJS-60, from Fuji Powdal, with a die opening diameter of 10 mmφ. Thus there were obtained solid pellets, 10 mmφ in diameter and 10-30 mm in average length.

The resulting pellets and the inorganic powder (according to the formulation shown in Table 5) were fed into the Fitz Mill together with dehumidified cold air at 15° C. (with a dew point of −5° C.). The flow rate was 5 $Nm^3$/min. Crushing was carried out at a throughput of 50 kg/hr. Two sets of Fitz Mill arranged in series were used. Fitz Mill is Model DKA-3 of Hosokawamicron. It has a fist-stage screen with an opening of 8 mmφ and a second-stage screen with an opening of 3.5 mmφ, and a first-stage blade rotating at 4700 rpm and a second-stage blade rotating at 2820 rpm. The resulting crushed product (powder) underwent aging under the condition shown in Table 5. Thus, there was obtained a powder containing α-sulfo fatty acid alkylester salt in high concentrations. The properties of the powder are shown in Table 5.

TABLE 5

| | Example | | | | | | |
|---|---|---|---|---|---|---|---|
| | 25 | 26 | 27 | 28 | 29 | 30 | 31 |
| Fatty acid methyl ester | A | A | A | A | A | A | A |
| Duration of aging of paste (hr) | 12 | 12 | 12 | 12 | 12 | 12 | 12 |
| Temperature of aging of paste (° C.) | 80 | 80 | 80 | 80 | 80 | 80 | 80 |
| Concentration of AI in paste (%) | 64.5 | 64.5 | 64.5 | 64.5 | 64.5 | 64.5 | 64.5 |
| Additive | polymer*7 1 | polymer*8 2 | polymer 1 | Tripoly | polymer 2 | Tripoly | CaO*9 |
| Amount of additive (% based on final product) | 10 | 5 | 5 | 25 | 10 | 15 | 5 |
| Water content in concentrates (%) | 3.5 | 1.8 | 2.3 | 1.6 | 2.0 | 2.0 | 2.0 |
| Inorganic powder used | ZeO | ZeO | ZeO | ZeO | ZeO | ZeO | ZeO |
| Average particle diameter of inorganic powder (μm) | 1 | 1 | 1 | 1 | — | 1 | 1 |
| Amount of inorganic powder (% based on final product) | 5 | 10 | 10 | 5 | — | 10 | 10 |
| Duration of aging of Powder (min) | 60 | 60 | 60 | 60 | 60 | 60 | 60 |
| Aging temperature (° C.) | 25 | 25 | 25 | 25 | 25 | 25 | 25 |
| Average particle diameter (μm) | 480 | 460 | 470 | 490 | 570 | 530 | 480 |
| Bulk density ($g/cm^3$) | 0.55 | 0.57 | 0.54 | 0.58 | 0.53 | 0.55 | 0.58 |
| Tendency to caking under pressure | ○ | ○ | ○ | ○ | ○ | ○ | ○ |
| Angle of repose | ○ | ○ | ○ | ○ | ○ | ○ | ○ |
| Color of particulate product | ○ | ○ | ○ | ○ | ○ | ○ | ○ |
| Odor | ○ | ○ | ○ | ○ | ○ | ○ | ○ |

*7 Polymer 1: Acrylic acid/maleic acid copolymer sodium
*8 Polymer 2: Sodium polyacrylate
*9 CaO: Calcium oxide

Examples 32 to 48

(Mixing with Other Particles)

The powder containing α-sulfo fatty acid alkylester salt which had been obtained in the foregoing examples was mixed with any one kind of particles 1 to 5 shown in Tables 6 to 11 according to the formulation shown in Tables 12 and 13. Mixing was accomplished by using a horizontal cylindrical rotary drum (400 mm in diameter, 700 mm long, and having an Fr number of 0.14). During mixing for 3 minutes, the mixture was sprayed with perfume. Thus there was obtained a granular detergent. The properties of the granular detergent are shown in Tables 12 and 13. The particles 1 to 5 which were added are explained later.

Composition and Preparation of Particles to be Mixed

<Particles 1>

A water-soluble alkaline inorganic salt as one of the components shown in Table 6 below was fed into a Loedige mixer (Model M-20, from Matsubo) equipped with plough-like shovels, with a clearance of 5 mm between the shovel and the wall surface, so that the packing fraction was 30 vol %. The main shaft was turned at 200 rpm, with the chopper remaining at rest. Ten seconds after the start of stirring, an aqueous solution of acrylic acid/maleic acid copolymer sodium was added over 30 seconds, and granulation and coating were carried out.

While the Loedige mixer was running, the lauric acid was added over 30 seconds, and coating was carried out. Then the zeolite was added and stirring was continued for 30 seconds. Thus there were obtained coated particles.

The coated particles were classified by using a sieve with an opening of 2000 μm. There were obtained particles 1 which had passed through the sieve.

TABLE 6

| Composition of particles 1 (wt % on net basis) | |
|---|---|
| Sodium carbonate[2] | 85.5 |
| Acrylic acid/maleic acid copolymer sodium | 3.0 |
| Lauric acid | 2.0 |
| Zeolite | 4.0 |
| Other minor components | Balance |
| Water content | 5.0 |
| Total | 100.0 |

<Particles 2>

The components (except for zeolite for coating) shown in Table 7 were mixed together according to the prescribed ratio to-give a slurry containing 40% water at 70° C. Incidentally, the LAS—K was formed in the slurry by feeding LAS—H and KOH into the reaction system.

The slurry was transferred to the top of the drying tower (2 m in diameter and 5 m in effective length) by the plunger pump. Then the slurry was sprayed into the tower through a pressure nozzle (at a pressure of 30 kg/cm$^2$) for drying. During spray-drying, the drying tower was kept at 260° C. (at the inlet of hot air) and 90-100° C. (at the outlet of discharged air). The powder collected from the bottom of the tower was mixed with zeolite for coating. Thus there was obtained the spray-dried powder.

The spray-dried powder, nonionic surfactant, and water in a ratio of 88.44:3.33:0.89 (by weight) were fed into the KRC kneader (Model S-4, from Kurimoto Tekkosho) to give a kneaded mixture at 60-70° C. The throughput was 180 kg/hr in terms of kneaded mixture. The kneaded mixture was fed into a pelleter having a die opening of 10 mmϕ (Model EXD-FJS-60, from Fuji Paudal). There were obtained solid pellets, 10 mmϕ in diameter and 10-30 mm in average length.

The resulting solid detergent in pellet form and zeolite in a ratio of 92.67:4.00 (by weight) were fed into the Fitz Mill together with cold air at 15° C. The flow rate was 6 Nm$^3$/min. Crushing was carried out at a throughput of 188 kg/hr. Three sets of Fitz Mill arranged in series were used. Fitz Mill is Model DKA-3 of Hosokawamicron. It has a fist-stage screen with an opening of 12 mmϕ, a second-stage screen with an opening of 6 mmϕ, and a third-stage screen with an opening of 2.3 mmϕ. It was run at a speed of 4700 rpm for all the stages.

The crushed particles were continuously fed, together with zeolite, into a horizontal cylindrical rotary tumbling drum (with an Fr number of 0.14, 0.70 m in diameter, 1.40 m long, inclined 3°, with 15 baffles, each measuring 1 mm thick, 50 mm high, and 350 mm long). The content in the rotary drum was sprayed with a nonionic surfactant. Thus there were obtained particles 2 as shown in Table 8. Incidentally, the ratio of the crushed product, the zeolite, and the nonionic surfactant sprayed each of which was fed into the rotary drum, was 96.67:3.00:0.33 (by weight).

TABLE 7

| Composition of spray-dried powder of particles 2 (wt % on net basis) | |
|---|---|
| LAS-K | 17.0 |
| AOS-K | 9.0 |
| Soap | 5.5 |
| Zeolite (added to slurry) | 21.0 |
| Zeolite (for coating) | 2.0 |
| Potassium carbonate | 11.0 |
| Sodium carbonate [2] | 24.0 |
| Fluorescent agent | 0.1 |
| Water content | 7.0 |
| Other minor components | Balance |
| Total | 100.0 |

TABLE 8

| Composition of particles 2 (wt % on net basis) | |
|---|---|
| LAS-K | 15.0 |
| AOS-K | 8.0 |
| Soap | 4.9 |
| Zeolite | 25.9 |
| Nonionic surfactant | 3.3 |
| Potassium carbonate | 9.7 |
| Sodium carbonate [2] | 21.2 |
| Fluorescent agent | 0.1 |
| Water content | 8.1 |
| Other minor components | Balance |
| Total | 100.0 |

<Particles 3>

The components (except for zeolite for coating) shown in Table 9 were mixed together according to the prescribed ratio to give a slurry containing 40% water at 70° C. Incidentally, the LAS—Na was formed in the slurry by feeding LAS—H and NaOH into the reaction system.

This slurry was spray-dried in the drying tower under the same condition as used for particles 2. The dried powder collected from the bottom of the tower was mixed with zeolite for coating. Thus there were obtained particles 3.

TABLE 9

| Composition of particles 3 (wt % on net basis) | |
|---|---|
| LAS-Na | 17.9 |
| AOS-Na | 4.0 |
| Sodium carbonate [2] | 9.8 |
| Calcium carbonate | 5.0 |
| Sodium tripolyphosphate | 14.9 |
| Sodium silicate | 11.9 |
| Zeolite (for coating) | 3.5 |
| Sodium sulfate | 24.7 |
| Water content | 7.0 |
| Other minor components | Balance |
| Total | 100.0 |

<Particles 4>

Of the components shown in Table 10 below, zeolite (main portion), white carbon, and sodium carbonate [1] were fed into a Loedige mixer (Model M-20, from Matsubo) equipped with plough-like shovels, with a clearance of 5 mm between the shovel and the wall surface, so that the packing fraction was 50 vol %. (Powder temperature: about 30° C.) For their mixing, the main shaft and chopper were turned at 200 rpm and 6000 rpm, respectively, for 30 seconds.

With the main shaft and chopper running for about 60 seconds, the powder mixture was incorporated with a mixture of nonionic surfactant and 12-hydroxystearic acid which had previously been prepared by melt-mixing at 85° C.

With the main shaft and chopper still running, the remaining portion of zeolite was added and mixing was continued for 90 seconds. Then, zeolite for coating was added and mixing was continued for 30 seconds. The resulting mixture was discharged from the Loedige mixer.

The thus obtained particles were sifted through a sieve with an opening of 2000 μm to give particles 4 as desired.

TABLE 10

| Composition of particles 4 (wt % on net basis) | |
|---|---|
| Nonionic surfactant | 23.0 |
| 12-hydroxystearic acid | 4.0 |
| Zeolite | 33.0<br>(main/remaining/coating = 24/5/4) |
| White carbon | 4.0 |
| Sodium carbonate [1] | 26.0 |
| Water content | 7.0 |
| Minor components | Balance |
| Total | 100.0 |

<Particles 5>

The components (except for zeolite for coating) shown in Table 11 were mixed together according to the prescribed ratio to give a slurry containing 50% water at 80° C. This slurry was spray-dried in the drying tower under the same condition as used for particles 2. The dried powder collected from the bottom of the tower was mixed with zeolite for coating. Thus there were obtained particles 5.

TABLE 11

| Composition of particles 5 (wt % on net basis) | |
|---|---|
| Soap | 30.0 |
| Sodium carbonate [2] | 40.0 |
| Potassium carbonate | 5.0 |
| Zeolite (for coating) | 17.0 |
| Water content | 6.0 |
| Minor components | Balance |
| Total | 100.0 |

TABLE 12

| | | Example | | | | | |
|---|---|---|---|---|---|---|---|
| | | 32 | 33 | 34 | 35 | 36 | 37 |
| Formulation (%) | Powder*[10] | 12.8<br>Example 1 | 25.5<br>Example 1 | 11.5<br>Example 6 | 26.0<br>Example 1 | 12.8<br>Example 1 | 12.8<br>Example 1 |
| | Particles 1 | — | — | — | — | 10.0 | 20.0 |
| | Particles 2 | 86.3 | 73.6 | — | — | 76.6 | 66.3 |
| | Particles 3 | — | — | 87.6 | 73.1 | — | — |
| | Particles 4 | — | — | — | — | — | — |
| | Particles 5 | — | — | — | — | — | — |
| | Enzyme | 0.7 | 0.7 | 0.7 | 0.8 | 0.3 | 0.7 |
| | Perfume | 0.2 | 0.2 | 0.2 | 0.1 | 0.3 | 0.2 |
| | Total | 100.0 | 100.0 | 100.0 | 100.0 | 100.0 | 100.0 |
| Properties | Angle of repose | ○ | ○ | ○ | ○ | ○ | ○ |
| | Tendency to caking under pressure | ○ | ○ | ○ | ○ | ○ | ○ |
| | Odor | ○ | ○ | ○ | ○ | ○ | ○ |

*[10]Powder containing α-sulfo fatty acid alkylester salt in high concentrations (upper line: content in percent, lower line: Example in which the powder was produced)

TABLE 13

| | | Example | | | | | |
|---|---|---|---|---|---|---|---|
| | | 38 | 39 | 40 | 41 | 42 | 43 |
| Formulation (%) | Powder*[10] | 25.5<br>Example 1 | 23.0<br>Example 6 | 15.0<br>Example 25 | 16.6<br>Example 30 | 12.8<br>Example 1 | 12.8<br>Example 1 |
| | Particles 1 | 10.0 | 20.0 | 10.0 | 10.0 | 67.1 | 47.0 |
| | Particles 2 | — | — | 74.8 | — | — | — |
| | Particles 3 | 64.2 | 56.8 | — | 73.2 | — | — |
| | Particles 4 | — | — | — | — | 20.0 | 20.0 |
| | Particles 5 | — | — | — | — | — | 20.0 |
| | Perfume | 0.3 | 0.2 | 0.2 | 0.2 | 0.1 | 0.2 |
| | Total | 100.0 | 100.0 | 100.0 | 100.0 | 100.0 | 100.0 |
| Properties | Angle of repose | ○ | ○ | ○ | ○ | ○ | ○ |

TABLE 13-continued

| | | Example | | | | | |
|---|---|---|---|---|---|---|---|
| | | 38 | 39 | 40 | 41 | 42 | 43 |
| | Tendency to caking under pressure | ○ | ○ | ○ | ○ | ○ | ○ |
| | Odor | ○ | ○ | ○ | ○ | ○ | ○ |

TABLE 14

| | | Example | | | | |
|---|---|---|---|---|---|---|
| | | 44 | 45 | 46 | 47 | 48 |
| Formulation (%) | Powder*[10] | 18.0 Example 18 | 12.8 Example 25 | 16.6 Example 30 | 12.5 Example 1 | 25.5 Example 1 |
| | Particles 1 | 41.6 | 37.0 | 43.1 | 20.0 | 20.0 |
| | Particles 2 | — | — | — | 27.3 | 24.3 |
| | Particles 3 | — | — | — | — | — |
| | Particles 4 | 20.0 | 20.0 | 20.0 | 20.0 | 20.0 |
| | Particles 5 | 20.0 | 30.0 | 20.0 | 20.0 | 10.0 |
| | Perfume | 0.4 | 0.2 | 0.3 | 0.2 | 0.2 |
| | Total | 100.0 | 100.0 | 100.0 | 100.0 | 100.0 |
| Properties | Angle of repose | ○ | ○ | ○ | ○ | ○ |
| | Tendency to caking under pressure | ○ | ○ | ○ | ○ | ○ |
| | Odor | ○ | ○ | ○ | ○ | ○ |

Example 49

The powder containing α-sulfo fatty acid alkylester salt in high concentrations and the components shown in Table 15 (except for nonionic surfactant for spraying and zeolite for coating) were fed into Plough-Shear Mixer (Model WB-75 from Pacific Machinery & Engineering), so that the α-sulfo fatty acid alkylester sodium (obtained in Example 1) as the active ingredient in the mixture was 10%. Their formulation is shown in Table 15. Granulation was carried out for 5 minutes, with the main shaft rotating at 162 rpm and the chopper rotating at 6000 rpm. Zeolite for coating was added such that the ratio of the granules to be obtained to the zeolite was 93.64:5.25 (by weight). After mixing for 1 minute, there were obtained granules. The granules were continuously fed into a horizontal cylindrical rotary drum (with an Fr number of 0.14, 0.70 m in diameter, 1.40 m long, inclined 3°, with 15 baffles, each measuring 1 mm thick, 50 mm high, and 350 mm long). The content in the rotary drum was sprayed with a nonionic surfactant for spraying. Those particles remaining on the sieve having an opening of 2 mmϕ were removed. Thus there was obtained the granular detergent as desired. Incidentally, the ratio of the granules (fed into the tumbling drum) to the nonionic surfactant for spraying was 98.89:1.11 (by weight). The properties of the granular detergent are shown in Table 15.

Examples 50 to 52

The powder containing α-sulfo fatty acid alkylester salt and the components shown in Table 15 (except for nonionic surfactant for spraying and zeolite for coating and as grind aid) were fed into KRC kneader (Model S-4, from Kurimoto), so that the α-sulfo fatty acid alkylester sodium (obtained in Example 1) as the active ingredient in the mixture was as shown in Table 15. Their formulation is shown in Table 15. (The nonionic surfactant and soap were those which had the form shown in Table 15.) There was obtained a kneaded mixture at 60-70° C. The throughput was 150 kg/hr in terms of mixture. The kneaded mixture was fed into a pelleter (Model EXDFJS-60, from Fuji Paudal) having a die diameter of 10 mmϕ. Thus there were obtained solid pellets, 10 mmϕ in diameter and 10-30 mm in average length.

The resulting solid pellets and zeolite (as a grinding aid) in a ratio of 91.76:5.25 (by weight) were fed into the Fitz Mill together with cold air at 15° C. The flow rate was 6 $Nm^3$/min. Crushing was carried out at a throughput of 160 kg/hr. Three sets of Fitz Mill arranged in series were used. Fitz Mill is Model DKA-3 of Hosokawamicron. It has a fist-stage screen with an opening of 6 mmϕ, a second-stage screen with an opening of 4 mmϕ, and a third-stage screen with an opening of 2 mmϕ, and a first-stage blade rotating at 1880 rpm, a second-stage blade rotating at 2350 rpm, and a third-stage blade rotating at 3760 rpm. Thus, there were obtained crushed particles.

The crushed particles were continuously fed, together with zeolite for coating, into a horizontal cylindrical rotary drum (with an Fr number of 0.14, 0.70 m in diameter, 1.40 m long, inclined 3°, with 15 baffles, each measuring 1 mm thick, 50 mm high, and 350 mm long). The content in the rotary drum was sprayed with a nonionic surfactant for spraying and perfume. Thus there was obtained the granular detergent as desired. Incidentally, the ratio of the crushed particles, the zeolite for coating, and the nonionic surfactant for spraying each of which was fed into the rotary drum, was 97.01:1.88:1.11 (by weight). The properties of the granular detergent are shown in Table 15.

TABLE 15

| Composition of granular detergent (wt % on net basis) | | Example 49 | 50 | 51 | 52 |
|---|---|---|---|---|---|
| Method of granulation | | Mixing Granulation | Kneading-crushing Granulation | Kneading-crushing Granulation | Kneading-crushing Granulation |
| α-sulfo fatty acid alkylester sodium | | 10.0 | 10.0 | 15.0 | 7.0 |
| Nonionic surfactant (as major ingredient/ for spraying) | | 4.0/1.0 | 4.0/1.0 | 3.0/1.0 | 8.0/1.0 |
| Soap | | 8.0 | 8.0 | 8.0 | 8.0 |
| Form of soap and nonionic surfactant*11 | | [1] | [1] | [2] | [3] |
| Zeolite (as major component/ as grind aid/for coating) | | 26.6/0.0/4.2 | 24.8/4.2/1.5 | 27.8/4.2/1.5 | 27.8/4.2/1.5 |
| Sodium sulfite | | 1.5 | 1.0 | 1.0 | 1.0 |
| Potassium carbonate | | 9.0 | 10.0 | 5.0 | 10.0 |
| Sodium carbonate [1] | | 22.0 | 23.4 | 20.6 | 17.5 |
| Water | | 7.5 | 5.8 | 6.8 | 8.9 |
| Perfume | | 0.4 | 0.3 | 0.3 | 0.3 |
| Other minor components | | Balance | Balance | Balance | Balance |
| Total | | 100.0 | 100.0 | 100.0 | 100.0 |
| Properties | Angle of repose | ○ | ○ | ○ | ○ |
| | Tendency to caking under pressure | ○ | ○ | ○ | ○ |
| | Odor | ○ | ○ | ○ | ○ |

*11 Form of soap and nonionic surfactant
[1] Nonionic surfactant: Aqueous solution containing 90% active ingredient; Soap: Particles containing 93% active ingredient.
[2] Nonionic surfactant/soap = concentrate of 3/8 mixture containing 8.1% water.
[3] Nonionic surfactant/soap = concentrate of 8/8 mixture containing 18.8% water

Example 53

The raw materials were mixed according to the formulation shown in Table 16 to give a slurry containing 40% water at 70° C. Incidentally, the LAS—K was formed in the slurry by feeding LAS—H and KOH into the reaction system. The α-sulfo fatty acid methylester sodium is the powder obtained in Example 1.

This slurry was spray-dried in the drying tower under the same condition as used for particles 2. The dried powder collected from the bottom of the tower was mixed with zeolite for coating. Thus there were obtained spray-dried particles. The properties of the spray-dried particles are shown in Table 16.

TABLE 16

| Composition and properties of spray-dried particles (wt % on net basis) | |
|---|---|
| α-sulfo fatty acid alkylester sodium | 11.8 |
| LAS-K | 9.4 |
| Soap | 10.6 |
| Maleic acid/acrylic acid copolymer sodium | 1.2 |
| Zeolite | 18.0 |
| Zeolite (for coating) | 2.1 |
| Sodium sulfite | 1.8 |
| Potassium carbonate | 10.6 |
| Sodium carbonate [2] | 26.1 |
| Water content | 4.5 |
| Other minor components | Balance |
| Total | 100.0 |

TABLE 16-continued

| Composition and properties of spray-dried particles (wt % on net basis) | |
|---|---|
| Angle of repose | ○ |
| Tendency to caking under pressure | ○ |
| Odor | ○ |

Example 54

The spray-dried particles obtained in Example 53, nonionic surfactant, and water in a ratio of 85.09:3.89:3.09 (by weight) were fed into KRC kneader (Model S-4, from Kurimoto). There was obtained a kneaded mixture at 60-70° C. The throughput was 180 kg/hr in terms of kneaded mixture. The kneaded mixture was fed into a pelleter (Model EXDFJS-60, from Fuji Paudal) having a die diameter of 10 mmϕ. Thus there were obtained solid pellets, 10 mmϕ in diameter and 10-30 mm in average length.

The resulting solid pellets and zeolite in a ratio of 92.07: 5.50 (by weight) were fed into the Fitz Mill together with cold air at 15° C. The flow rate was 6 $Nm^3$/min. Crushing was carried out at a throughput of 190 kg/hr. Three sets of Fitz Mill arranged in series were used. Fitz Mill is Model DKA-3 of Hosokawamicron. It has a fist-stage screen with an opening of 12 mmϕ, a second-stage screen with an opening of 6 mmϕ, and a third-stage screen with an opening of 2.5 mmϕ, and all the stages running at 4700 rpm. Thus, there were obtained crushed particles.

The crushed particles were continuously fed, together with zeolite, into a horizontal cylindrical rotary drum (with an Fr number of 0.14, 0.70 m in diameter, 1.40 m long, inclined 3°, with 15 baffles, each measuring 1 mm thick, 50 mm high, and 350 mm long). The content in the rotary drum was sprayed with a nonionic surfactant. Thus there was obtained the granular detergent as desired. Incidentally, the ratio of the crushed particles, the zeolite, and the nonionic surfactant sprayed each of which was fed into the rotary drum, was 97.57:1.88:0.55 (by weight). The properties of the granular detergent are shown in Table 17.

TABLE 17

| Composition and properties of granular detergent (wt % on net basis) | |
|---|---|
| α-sulfo fatty acid alkylester sodium | 10.0 |
| LAS-K | 8.0 |
| Nonionic surfactant | 4.0 |
| Soap | 9.0 |
| Maleic acid/acrylic acid copolymer sodium | 1.0 |
| Zeolite | 23.0 |
| Sodium sulfite | 1.5 |
| Potassium carbonate | 9.0 |
| Sodium carbonate [2] | 22.2 |
| Water content | 8.1 |
| Other minor components | Balance |
| Total | 100.0 |
| Angle of repose | ○ |
| Tendency to caking under pressure | ○ |
| Odor | ○ |

Example 55

The spray-dried particles obtained in Example 53, nonionic surfactant, and water in a ratio of 88.66:3.89:1.39 (by weight) were fed into Plough-Shear Mixer (Model WB-75 from Pacific Machinery & Engineering). Granulation was carried out for 5 minutes, with the main shaft rotating at 162 rpm and the chopper rotating at 6000 rpm. Zeolite was added such that the ratio of the granules to the zeolite was 93.94:5.50 (by weight). After mixing for 1 minute, there were obtained granules. The granules were continuously fed into a horizontal cylindrical rotary drum (with an Fr number of 0.14, 0.70 m in diameter, 1.40 m long, inclined 3°, with 15 baffles, each measuring 1 mm thick, 50 mm high, and 350 mm long). The content in the tumbling drum was sprayed with a nonionic surfactant. Those particles remaining on the sieve having an opening of 2 mmφ were removed. Thus there was obtained the granular detergent as desired. Incidentally, the ratio of the granules to the nonionic surfactant sprayed each of which was fed into the rotary drum, was 99.44:0.56 (by weight). The properties of the granular detergent are shown in Table 18.

TABLE 18

| Composition and properties of granular detergent (wt % on net basis) | |
|---|---|
| α-sulfo fatty acid alkylester sodium | 10.5 |
| LAS-K | 8.3 |
| Nonionic surfactant | 4.0 |
| Soap | 9.4 |
| Maleic acid/acrylic acid copolymer sodium | 1.1 |
| Zeolite | 22.2 |
| Sodium sulfite | 1.6 |
| Potassium carbonate | 9.4 |
| Sodium carbonate [2] | 23.1 |
| Water content | 6.3 |
| Other minor components | Balance |
| Total | 100.0 |
| Angle of repose | ○ |
| Tendency to caking under pressure | ○ |
| Odor | ○ |

Examples 56 to 66

The raw materials and particles in a ratio shown in Tables 22 to 24 were fed into a horizontal cylindrical rotary drum (400 mm in diameter, 700 mm long, with an Fr number of 0.3). Mixing was carried out for 2 minutes, while spraying with perfume and water. The resulting mixture was fed into KRC kneader (Model S-4, from Kurimoto), and mixed. The resulting mixture was fed into a pelleter (Model EXDFJS-60, from Fuji Paudal) having a die diameter of 100 mmφ. Thus there were obtained solid pellets. The solid pellets were mixed and formed into a solid detergent by using a vacuum two-stage prodder (from Nippon Kakoki). The each resulting solid detergent was satisfactory in productivity and quality (detergency). Incidentally, the particles 6 to 17 were obtained by the following process.

Composition and Preparation of Particles to be Mixed

<Particles 6 to 10>

The raw materials were mixed according to the formulation shown in Table 19 to give a slurry containing 40% water at 70° C. Incidentally, the LAS—Na was formed in the slurry by feeding LAS—H and NaOH into the reaction system.

The resulting slurry was spray-dried under the same condition as used for particles 2. Dried particles were collected from the bottom of the tower. Thus there were obtained particles 6 to 10.

TABLE 19

| Composition (%) | Particles 6 | Particles 7 | Particles 8 | Particles 9 | Particles 10 |
|---|---|---|---|---|---|
| LAS-Na | 7.8 | 11.7 | 12.3 | 0.0 | 0.0 |
| AOS-Na | 4.5 | 4.3 | 4.9 | 6.0 | 0.0 |
| Sodium tripolyphosphate | 11.2 | 10.6 | 9.9 | 12.0 | 11.0 |
| Calcium carbonate | 11.2 | 10.6 | 9.9 | 12.0 | 11.0 |
| Sodium carbonate | 19.0 | 16.0 | 18.5 | 20.0 | 20.0 |
| Sodium sulfate | 39.1 | 39.4 | 37.0 | 42.0 | 50.0 |
| Fluorescent whitening agent | 0.01 | 0.01 | 0.01 | 0.02 | 0.02 |
| Other minor components | Balance | Balance | Balance | Balance | Balance |
| Water content | 4.2 | 4.7 | 4.5 | 5.0 | 4.9 |
| Total | 100.0 | 100.0 | 100.0 | 100.0 | 100.0 |

<Particles 11 to 14>

The raw materials (except for MES, LAS—H, and AOS—Na) according to the formulation shown in Table 20 were fed into a Loedige mixer (Model M-20, from Matsubo) equipped with plough-like shovels, with a clearance of 5 mm between the shovel and the wall surface, so that the packing fraction was 30 vol %. Mixing was carried out, with the main shaft and chopper rotating at 200 rpm and 3000 rpm, respectively. Thirty seconds after the start of mixing, a solution of LAS—H was added for 2 minutes.

While mixing was continued, a solution of AOS—Na was added for 1 minute and then MES (shown in Table 20) was added. Mixing was continued for 1 minute. There were obtained particles.

The thus obtained particles were sifted through a sieve with an opening of 2000 μm to give particles 11 to 14.

TABLE 20

(wt % on net basis except for MES)

| Composition (%) | Particles 11 | Particles 12 | Particles 13 | Particles 14 |
|---|---|---|---|---|
| MES*[12] | — | — | — | 10.0<br>Example 1 |
| LAS-Na | 7.7 | 7.9 | 18.0 | 10.0 |
| AOS-Na | 4.4 | — | 7.0 | 6.0 |
| Sodium tripolyphosphate | 11.0 | 11.3 | 10.0 | 10.0 |
| Calcium carbonate | 11.0 | 11.3 | 10.0 | 10.0 |
| Sodium carbonate | 18.7 | 19.2 | 15.0 | 16.0 |
| Sodium sulfate | 38.5 | 39.5 | 30.0 | 27.9 |
| Fluorescent whitening agent | 0.01 | 0.01 | 0.01 | — |
| Other minor components | Balance | Balance | Balance | Balance |
| Water content | 6.1 | 8.0 | 7.3 | 7.6 |
| Total | 100.0 | 100.0 | 100.0 | 100.0 |

*[12]The powder flakes, or pellets containing α-sulfo fatty acid alkylester salt in high concentrations, (upside: formulation, downside: Applicable example)

<Particles 15 and 16>

The raw materials (except for MES, LAS—H, and AOS—Na) according to the formulation shown in Table 21 were fed into a Loedige mixer (Model M-20, from Matsubo) equipped with plough-like shovels, with a clearance of 5 mm between the shovel and the wall surface, so that the packing fraction was 30 vol %. Mixing was carried out, with the main shaft and chopper rotating at 200 rpm and 3000 rpm, respectively. Thirty seconds after the start of mixing, a mixture of a solution of LAS—H and a solution of AOS—Na was added for 3 minutes. Then MES shown in Table 21 was added. Mixing was continued for 1 minute. There were obtained particles.

The thus obtained particles were sifted through a sieve with an opening of 2000 μm to give particles 15 and 16.

<Particles 17>

The raw materials (except for MES, LAS—H, and AOS—Na) according to the formulation shown in Table 21 were fed into a Loedige mixer (Model M-20, from Matsubo) equipped with plough-like shovels, with a clearance of 5 mm between the shovel and the wall surface, so that the packing fraction was 30 vol %. Mixing was carried out for 30 seconds, with the main shaft and chopper rotating at 200 rpm and 3000 rpm, respectively. With mixing suspended temporarily, a mixture of a solution of LAS—H and a solution of AOS—Na was added for 15 seconds. Mixing was continued for 2 minutes under the above-mentioned condition. Then MES shown in Table 21 was added. Mixing was continued for 1 minute. There were obtained particles.

The thus obtained particles were sifted through a sieve with an opening of 2000 μm to give particles 17.

TABLE 21

(wt % on net basis except for MES)

| Composition (%) | Particles 15 | Particles 16 | Particles 17 |
|---|---|---|---|
| MES*[12] | 10.0<br>Example 6 | — | 7.1<br>Example 10 |
| LAS-Na | 10.6 | 10.0 | 8.2 |
| AOS-Na | — | 6.0 | 4.1 |
| Sodium tripolyphosphate | 12.0 | — | 11.2 |
| Calcium carbonate | 12.0 | — | 11.2 |
| Sodium carbonate | 18.0 | 25.0 | 16.3 |
| Sodium sulfate | 27.9 | 50.0 | 32.4 |
| Fluorescent whitening agent | — | 0.02 | 0.01 |
| Other minor components | Balance | Balance | Balance |
| Water content | 7.6 | 6.2 | 7.0 |
| Total | 100.0 | 100.0 | 100.0 |

*[12]Powder, flakes, or pellets containing α-sulfo fatty acid alkylester salt in high concentrations (upper line: formulation, lower line: manufacturing method)

TABLE 22

| Formulation (wt %) | Example 56 | Example 57 | Example 58 | Example 59 |
|---|---|---|---|---|
| Particles 6 | 89.5 | 53.3 | — | — |
| Particles 7 | — | — | 94.0 | — |
| Particles 8 | — | — | — | 78.1 |
| MES*[12] | 7.0<br>Example 1 | 8.0<br>Example 10 | 3.0<br>Example 1 | 15.0<br>Example 14 |
| Sodium tripolyphosphate | — | 4.0 | — | — |
| Calcium carbonate | — | 4.0 | — | — |
| Sodium carbonate | — | 6.9 | — | — |
| Sodium sulfate | — | 17.6 | — | — |
| Perfume | 0.3 | 0.3 | 0.2 | 0.3 |
| Pigment | 0.02 | 0.02 | 0.01 | 0.02 |
| Other minor components | Balance | Balance | Balance | Balance |
| Water content (excluding water brought in by particles) | 2.9 | 4.5 | 2.7 | 3.8 |
| Total | 100.0 | 100.0 | 100.0 | 100.0 |

TABLE 23

| Formulation (wt %) | Example 60 | Example 61 | Example 62 | Example 63 |
|---|---|---|---|---|
| Particles 6 | 53.0 | — | — | — |
| Particles 9 | — | — | — | 28.0 |
| Particles 10 | — | 38.9 | 29.3 | — |
| Particles 12 | 24.0 | — | — | — |
| Particles 13 | — | 55.5 | — | — |
| Particles 14 | — | — | 70.0 | — |
| Particles 15 | — | — | — | 70.0 |
| MES*[12] | 8.0<br>Example 1 | 4.0<br>Example 13 | — | — |
| Sodium sulfate | 11.5 | — | — | — |
| Perfume | 0.3 | 0.2 | 0.3 | 0.3 |
| Pigment | 0.02 | 0.01 | 0.02 | 0.02 |
| Other minor components | Balance | Balance | Balance | Balance |
| Water content (excluding water brought in by particles) | 2.7 | 1.2 | 0.3 | 1.4 |
| Total | 100.0 | 100.0 | 100.0 | 100.0 |

TABLE 24

| Formulation (wt %) | Example 64 | Example 65 | Example 66 |
|---|---|---|---|
| Particles 11 | 90.9 | — | — |
| Particles 16 | — | 65.0 | — |
| Particles 17 | — | — | 98.0 |
| MES*[12] | 7.0 Example 11 | 4.0 Example 1 | — |
| Sodium tripolyphosphate | — | 13.0 | — |
| Calcium carbonate | — | 13.0 | — |
| Perfume | 0.3 | 0.2 | 0.3 |
| Pigment | 0.02 | 0.02 | 0.02 |
| Other minor components | Balance | Balance | Balance |
| Water content | 1.5 | 4.0 | 0.6 |
| Total | 100.0 | 100.0 | 100.0 |

The raw materials used in Examples and Comparative Examples are shown below.

(1) Fatty Acid Methyl Ester

Fatty acid methyl ester as the raw material was prepared from esterified palm oil (which is fatty acid methyl ester available under a trade name of A, C: Edenor ME PA MY (from Cognis) and B: 2:8 (by weight) mixture of Paster M-14 and Paster M-16 (from Lion Oleo chemical) by hydrogenation to reduce the iodine value for purification. Hydrogenation was carried out in the usual way in the presence of a catalyst ("SO-850" from Sakai Chemical Industry) (0.15% for the fatty acid methyl ester) at 170° C. for 8 hours. Table 25 shows the carbon distribution and properties of the fatty acid methyl ester-as the raw material.

TABLE 25

| | | A Cognis | B Lion Oleo Chemical | C Cognis |
|---|---|---|---|---|
| Long-chain Distribution (%) | $C_{10}$ | 0-1 | 0-1 | 0-1 |
| | $C_{12}$ | 0-1 | 0-1 | 0-1 |
| | $C_{14}$ | 1-2 | 18-22 | 1-2 |
| | $C_{16}$ | 40-45 | 78-82 | 40-45 |
| | $C_{17}$ | — | 0-2 | — |
| | $C_{18}$ | 50-55 | 0-1 | 50-55 |
| | $C_{20}$ | 0-1 | — | 0-1 |
| Acid value | | Equal to or less than 1 | Equal to or less than 1 | Equal to or less than 1 |
| Unsaponified material | | Equal to or less than 1 | Equal to or less than 1 | Equal to or less than 1 |
| Water content | | Equal to or less than 0.5% | Equal to or less than 0.5% | Equal to or less than 0.5% |
| Iodine value | | 0.03 | 0.05 | 0.49 |
| Average molecular weight | | 285 | 264 | 285 |

(2) Sulfonating gas: produced from $SO_2$ by catalytic oxidation with dry air (with a dew point of −55° C.).

(3) LAS—H: "Lipon LH-200" from Lion. Linear alkylbenzenesulfonic acid having a $C_{10-14}$ alkyl group (96% active ingredient, with the balance being unreacted alkylbenzene, sodium sulfate, water, etc.). To be used as LAS—Na or LAS—K.

(4) AOS—K: A 7:3 mixture of potassium a-olefin sulfonate and potassium hydroxyalkylsulfonate (70% net, with the balance being unreacted α-olefin, sodium sulfate, sultone, sodium hydroxide, and water, etc). The olefin is a mixture composed of $C_{14}$:$C_{16}$:$C_{18}$=15:50:35.

(5) AOS—Na: "Liporan LB-440" from Lion.

(6) Soap: Fatty acid sodium salt in which $C_{16}$:$C_{18}$:TMD (mixture of C10-20 esters)=1:3:1 (67% active ingredient).

(7) Nonionic surfactant: An alcohol ethoxylate which is adducted of $C_{12-13}$ alcohol with 15 mol (on average) of ethylene oxide (90% purity, with the balance being unreacted alcohol, PEG (polyethylene glycol), water, etc.).

(8) Methanol: Methanol (extra pure reagent) from Junsei Kagaku.

(9) Sodium hydroxide: Flaky sodium hydroxide for food additive, from Asahi Glass.

(10) Potassium hydroxide: Flaky potassium hydroxide for food additive, from Asahi Glass.

(11) Hydrogen peroxide: 35% aqueous solution of hydrogen peroxide (extra pure reagent), from Junsei Chemical.

(12) Sodium carbonate [1]: Powder having an average particle diameter of 10-60 μm, obtained by crushing from light soda ash having a purity of 99% and a bulk density of 0.55 g/cm$^3$, from Asahi Glass.

(13) Sodium carbonate [2]: Granular soda ash having a purity of 99% and a bulk density of 1.07 g/cm$^3$, from Asahi Glass.

(14) Potassium carbonate: Food additive grade in crushed form having a purity of 99% and a bulk density of 0.77 g/cm$^3$, from Asahi Glass.

(15) Sodium tripolyphosphate: Food additive grade, having a purity of 85% and a bulk density of 0.97 g/cm$^3$, from Taihei Chemical Industry.

(16) Zeolie: A type zeolite having a bulk density of 0.30 g/cm$^3$, "Silton B" from Mizusawa Chemical.

(17) Sodium sulfate : Neutral anhydrous sodium sulfate in the form of fine powder having an average particle diameter of 40-50 μm, technical grade, from Shikoku Corp.

(18) Potassium sulfate: In the form of fine powder having a particle diameter of 20-30 μm, from Ueno Fine Chemical Industry.

(19) Calcium carbonate: Guaranteed reagent, from Junsei Chemical.

(20) Sodium sulfite: Anhydrous sodium sulfite from K. K. Kamisu Kagaku Kogyo-sho.

(21) Maleic acid/acrylic acid copolymer sodium: "Aquaric TL-400" in the form of 40% aqueous solution, from Nippon Shokubai.

(22) Sodium polyacrylate: "Aquaric DL-100", from Nippon Shokubai.

(23) White carbon: "Tokuseal N" from Tokuyama.

(24) Sodium citrate: Trisodium citrate dehydrate, extra pure, from Junsei Chemical.

(25) Calcium oxide: Calcium oxide powder, guaranteed reagent, from Showa chemical Industry.

(26) 12-hydroxystearic acid: 85% purity, from K F Trading.

(27) Lauric acid: NAA-122 from NOF Corp.

(28) Enzyme: Protease-lipase mixed enzyme, from Novonoldisc.

(29) Perfume: Perfume composition A shown in Tables 11 to 18 in Japanese Patent Laid-open No. 2002-146399.

(30) Pigment: Ultramarine, from Dainichiseika Color & Chemicals Mfg.

(31) Fluorescent whitening agent: AMS-GX from Ciba Specialty Chemicals.

The invention claimed is:

1. A process for producing a granular detergent comprising:

(1) a step of preparing a paste containing α-sulfo fatty acid alkylester salt by a series of reactions of sulfonating a fatty acid alkylester with a sulfonating gas by contact with each other, esterifying the sulfonated product with a lower alcohol, neutralizing the esterified product, and bleaching the neutralized, product, to give a paste containing α-sulfo fatty acid alkylester salt;

(2) a step of conducting a first aging of the thus obtained paste, wherein the first aging temperature is 60-90° C. and the first aging time is 1-48 hours:

(3) a step of making the aged paste into flakes or pellets containing equal to or less than 10 wt % of water, or a step of making the aged paste into flakes or pellets containing equal to or less than 10 wt % of water and then crushing the resulting flakes or pellets into a powder having an average particle diameter of 100-1500 μm;

(4) a step of conducting a second aging of the powder, flakes, or pellets, wherein the second aging temperature is 25-45° C. and the second aging time is equal to or longer than 30 minutes; and (5) a step of mixing or granulating the powder, flakes, or pellets obtained by the above step (4) with a detergent component by any method selected from powder mixing, kneading-crushing, and agitation granulation.

2. The process as defined in claim 1, wherein the second aging temperature is 30-45° C.

3. The process as defined in claim 1, wherein the second aging temperature is 30-40° C.

4. The process as defined in claim 1, wherein the first aging time is 2-12 hours.

5. A process for producing a granular detergent comprising:

(1) a step of preparing a paste containing α-sulfo fatty acid alkylester salt by a series of reactions of sulfonating a fatty acid alkylester with a sulfonating gas by contact with each other, esterifying the sulfonated product with a lower alcohol, neutralizing the esterizfied product, and bleaching the neutralized product, to give a paste containing α-sulfo fatty acid alkylester salt;

(2) a step of conducting a first aging of the thus obtained paste, wherein the first aging temperature is 60-90° C. and the first aging time is 1-48 hours;

(3) a step of making the aged paste into flakes or pellets containing equal to or less than 10 wt % of water, or a step of making the aged paste into flakes or pellets containing equal to or less than 10 wt % of water and then crushing the resulting flakes or pellets into a powder having an average particle diameter of 100-1500 μm;

(4) a step of conducting a second aging of the powder, flakes, or pellets, wherein the second aging temperature is 25-45° C. and the second aging time is equal to or longer than 30 minutes; and (5) a step of mixing the powder, flakes, or pellets obtained by the above step (4) with a detergent component and water, to give a slurry containing 20-50 wt % of water, and spray-drying the slurry.

6. The process as defined in claim 5, wherein the second aging temperature is 30-45° C.

7. The process for producing a granular detergent defined in claim 1 or 5, further comprising a step of mixing or granulating the granular detergent obtained by the process defined in claim 1 or 5 with a detergent component by any method selected from powder mixing, kneading-crushing, and agitation granulation.

8. A process for producing a solid detergent comprising:

(1) a step of preparing a paste containing α-sulfo fatty acid alkylester salt by a series of reactions of sulfonating a fatty acid alkylester with a sulfonating gas by contact with each other, esterifying the sulfonated product with a lower alcohol, neutralizing the esterilied product, and bleaching the neutralized product, to give a paste containing α-sulfo fatty acid alkylester salt;

(2) a step of conducting a first aging of the thus obtained paste wherein the first aging temperature is 60-90° C. and the first aging time is 1-48 hours;

(3) a step of making the aged paste into flakes or pellets containing equal to or less than 10 wt % of water, or a step of making the aged paste into flakes or pellets containing equal to or less than 10 wt % of water and then crushing the resulting flakes or pellets into a powder having an average particle diameter of 100-1500 μm;

(4) a step of conducting a second aging of the powder, flakes, or pellets, wherein the second aging temperature is 25-45° C. and the second aging time is equal to or longer than 30 minutes; and (5) a step of mixing and kneading the powder, flakes, or pellets obtained by the above step (4) with a detergent component, to obtain solid detergent.

9. The process as defined in claim 8, wherein the second aging temperature is 30-45° C.

10. A process for producing a granular detergent comprising:

(1) a step of preparing a paste containing α-sulfo fatty acid alkylester salt by a series of reactions of sulfonating a fatty acid alkylester with a sulfonating gas by contact with each other, esterifying the sulfonated product with a lower alcohol, neutralizing the esterified product, and bleaching the neutmilized product, to give a paste containing α-sulfo fatty acid alkylester salt;

(2) a step of conducting a first aging of the thus obtained paste, wherein the first aging temperature is 60-90° C. and the first aging time is 1-48 hours;

(3) a step of making the aged paste into flakes or pellets containing equal to or less than 10 wt % of water, or a step of making the aged paste into flakes or pellets containing equal to or less than 10 wt % of water and then crushing the resulting flakes or pellets into a powder having an average particle diameter of 100-1500 μm;

(4) a step of conducting a second aging of the powder, flakes, or pellets, wherein the second aging temperature is 25-45° C. and the second aging time is equal to or longer than 30 minutes; and (5) a step of mixing the powder, flakes, or pellets obtained by the above step (4) with detergent particles by powder mixing.

11. The process as defined in claim 10, wherein the second aging temperature is 30-45° C.

* * * * *